US008728813B2

(12) United States Patent
Efrat et al.

(10) Patent No.: US 8,728,813 B2
(45) Date of Patent: May 20, 2014

(54) METHODS OF EXPANDING AND REDIFFERENTIATING ISLET BETA CELLS

(75) Inventors: Shimon Efrat, Zikhron-Yaakov (IL); Yael Bar, Tel-Aviv (IL); Holger A. Russ, Boeblingen (DE)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/338,453

(22) Filed: Dec. 28, 2011

(65) Prior Publication Data

US 2012/0121560 A1 May 17, 2012

Related U.S. Application Data

(63) Continuation-in-part of application No. PCT/IL2011/000738, filed on Sep. 15, 2011.

(60) Provisional application No. 61/487,782, filed on May 19, 2011, provisional application No. 61/382,956, filed on Sep. 15, 2010.

(51) Int. Cl.
| C12N 5/00 | (2006.01) |
| C12N 5/02 | (2006.01) |
| C12N 15/00 | (2006.01) |
| A61K 38/00 | (2006.01) |
| C12N 15/11 | (2006.01) |
| A61K 48/00 | (2006.01) |

(52) U.S. Cl.
USPC ........... 435/377; 435/404; 435/455; 435/325; 514/5.9; 514/44 R; 514/44 A

(58) Field of Classification Search
None
See application file for complete search history.

(56) References Cited

U.S. PATENT DOCUMENTS

| 2002/0164307 A1 | 11/2002 | Habener et al. |
| 2006/0292127 A1 | 12/2006 | Kulkarni et al. |
| 2010/0278789 A1 * | 11/2010 | Efrat et al. ................... 424/93.7 |

FOREIGN PATENT DOCUMENTS

| WO | WO 2006/054305 | 5/2006 |
| WO | WO 2009/078012 | 6/2009 |
| WO | WO 2012/035539 | 3/2012 |

OTHER PUBLICATIONS

Liew. Generation of Insulin-Producing Cells from Pluripotent Stem Cells: From the Selection of Cell Sources to the Optimization of Protocols. The Review of Diabetic Studies. 2010. 7(2) 82-92.*
Stadfeld et al. Reprogramming of Pancreatic Beta Cells into Induced Pluripotent Stem Cells. Current Biology, 2008. 18(12):890-894.*
Davani et al. "Human Islet-Derived Precursor Cells Are Mesenchymal Stromal Cells That Differentiate and Mature to Hormone-Expressing Cells In Vivo", Stem Cells, 25(12): 3215-3222, Dec. 2007.
Rukstalis et al. "Transcription Factor Snail Modulates Hormone Expression in Established Endocrine Pancreatic Cell Lines", Endocrinology, 147(6): 2997-3006, 2006.
International Search Report and the Written Opinion Dated Feb. 9, 2012 From the International Searching Authority Re. Application No. PCT/IL2011/000738.
Banerjee et al. "A Simple Two-Step Protocol for the Purification of Human Pancreatic Beta Cells", Diabetologia, XP019698534, 52(4): 621-625, Jan. 24, 2009.
Bar et al. "HES-1 Is Involved in Adaption of Adult Human Beta-Cells to Proliferation In Vitro", Diabetes, XP002564760, 57(9): 2413-2420, Sep. 1, 2008. R-h Col., p. 2419, r-h Col., Para 4.
Bar-Nur et al. "Epigenetic Memory and Preferential Lineage-Specific Differentiation in Induced Pluripotent Stem Cells Derived From Human Pancreatic Islet Beta Cells", Stem Cell Stem, XP028097462, 9(1): 17-23, Jun. 10, 2011.
Lukowiak et al. "Identification and Purification of Functional Human Beta-Cells by a New Specific Zinc-Fluorescent Probe", The Journal of Histochemistry & Cytochemistry, XP001053775, 49(4): 519-527, Apr. 1, 2001.
Ouziel-Yahalom et al. "Expansion and Redifferentiation of Adult Human Pancreatic Islet Cells", Biochemical and Biophysical Research Communications, XP024923871, 341(2): 291-298, Mar. 10, 2006. p. 292, p. 295-297.
Ramiya et al. "Reversal of Insulin-Dependent Diabetes Using Islets Generated In Vitro From Pancreatic Stem Cells", Nature Medicine, XP000864764, 6(3): 278-282, Mar. 1, 2000. p. 279, Para 2—p. 280, l-h Col.
Russ et al. "Insulin-Producing Cells Generated From Dedifferentiated Human Pancreatic Beta Cells Expanded In Vitro", PLoS One, XP055016789, 6(9): e25566-1-e25566-12, Jan. 1, 2011.
International Preliminary Report on Patentability Dated Mar. 28, 2013 From the International Bureau of WIPO Re. Application No. PCT/IL2011/000738.

* cited by examiner

*Primary Examiner* — Joseph Woitach
*Assistant Examiner* — Kimberly A Aron

(57) ABSTRACT

A method of ex-vivo increasing insulin content in progenitor cells which express SLUG is provided. The method comprises downregulating an amount or activity of SLUG in the progenitor cells. Cell populations generated thereby and uses thereof are also provided.

4 Claims, 17 Drawing Sheets
(14 of 17 Drawing Sheet(s) Filed in Color)

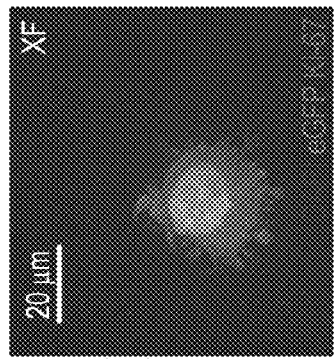
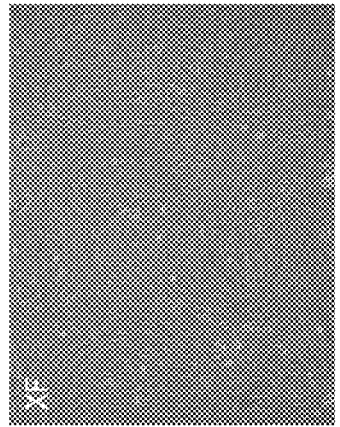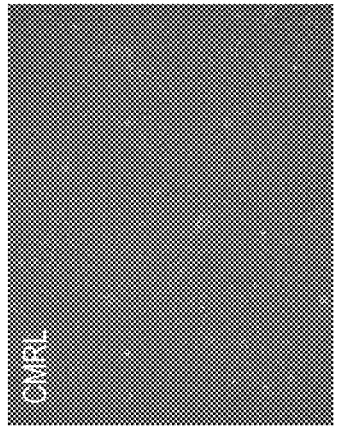
FIG. 1A    FIG. 1B

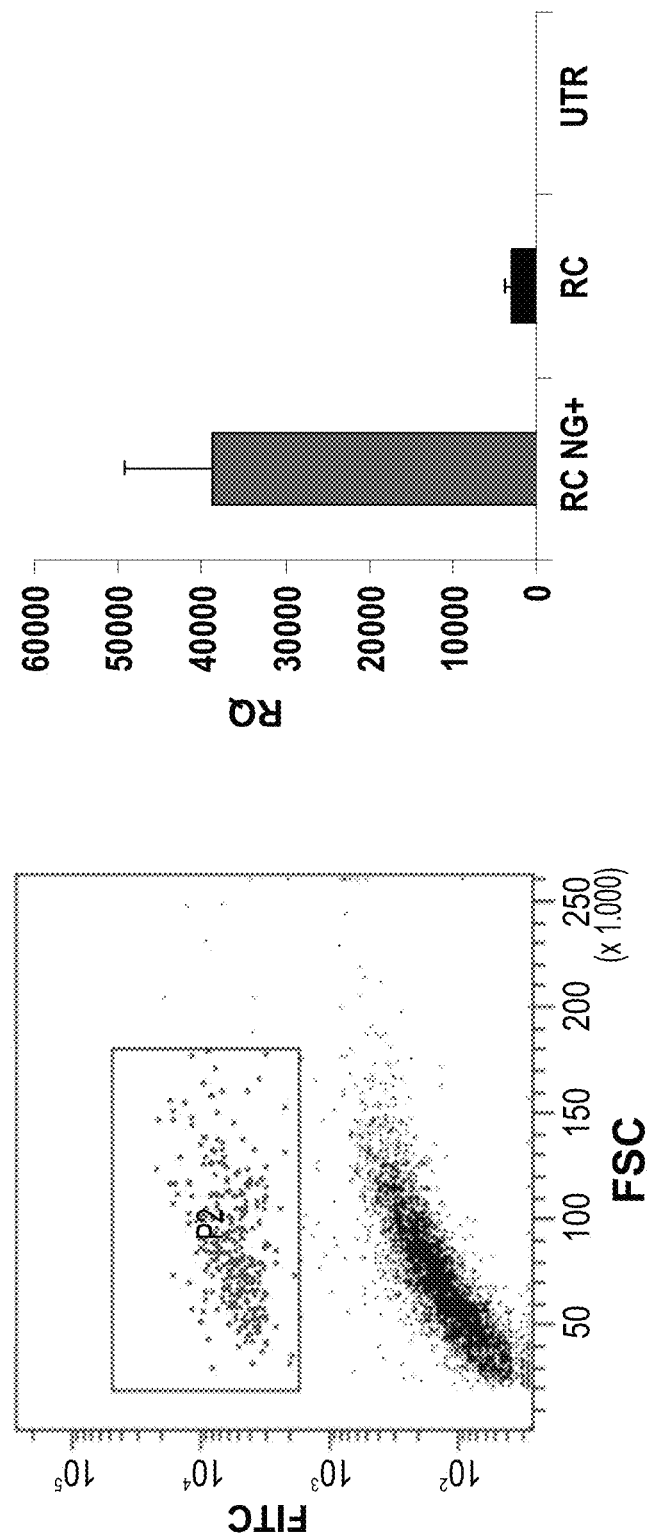

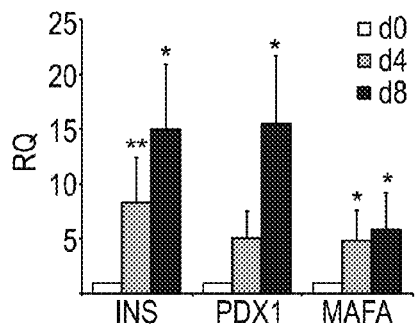
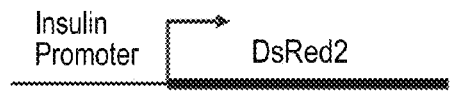
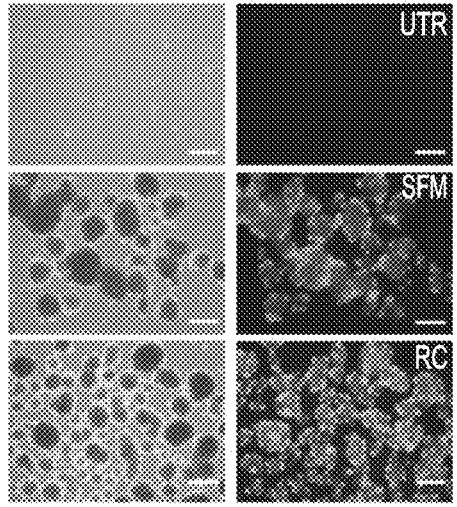
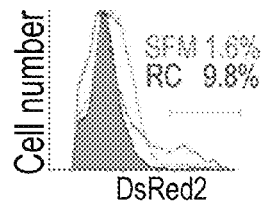
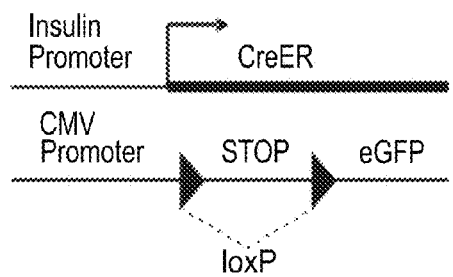
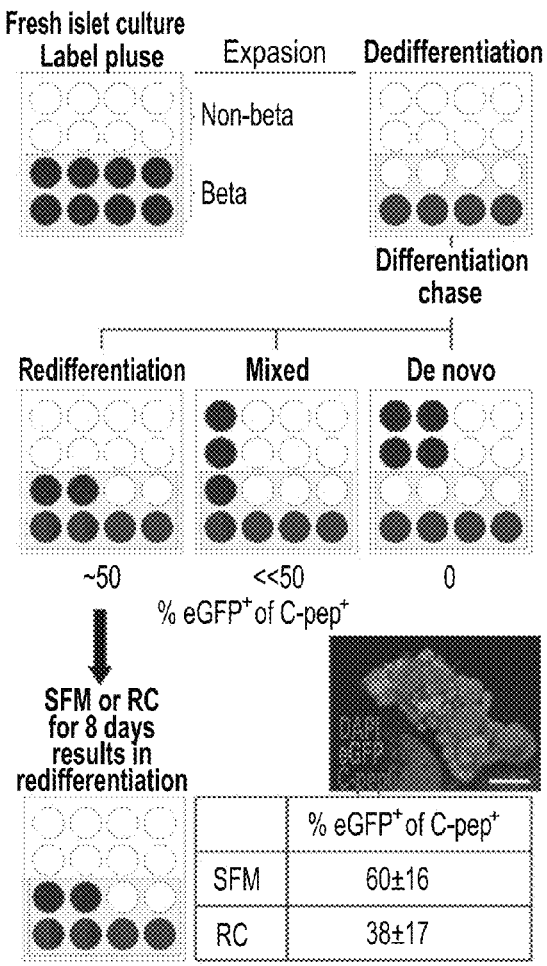

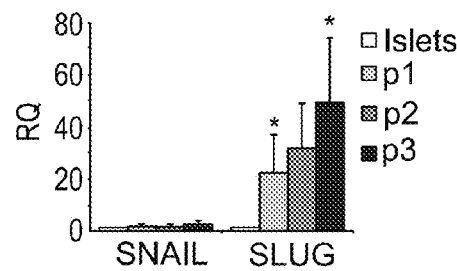
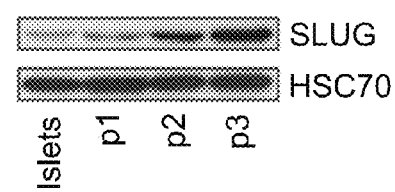
FIG. 10A  FIG. 10B
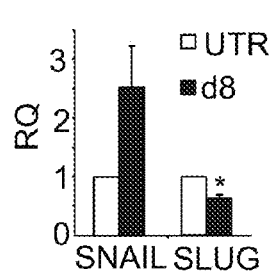
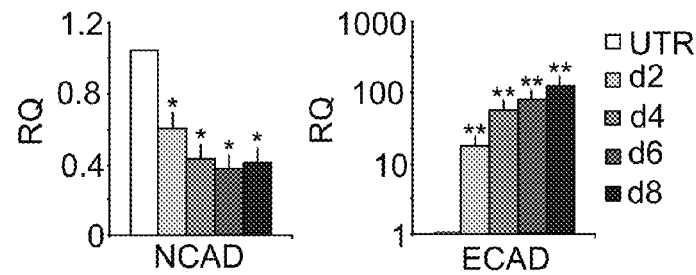
FIG. 10C  FIG. 10D
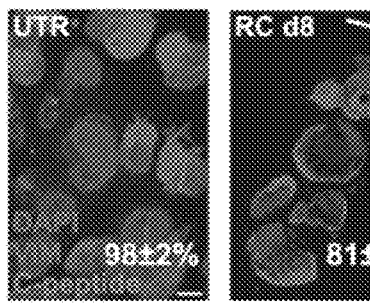
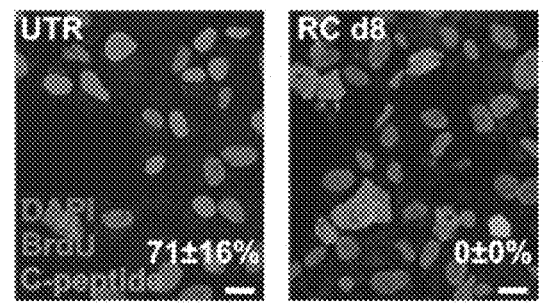
FIG. 10E  FIG. 10F
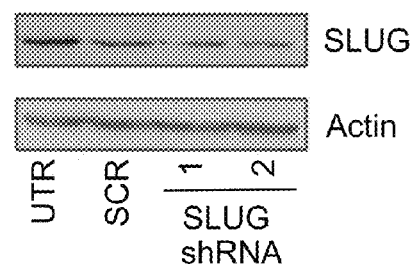
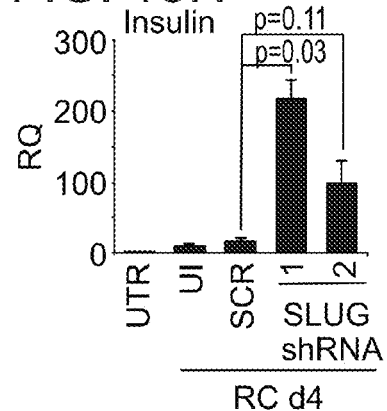
FIG. 10G  FIG. 10H

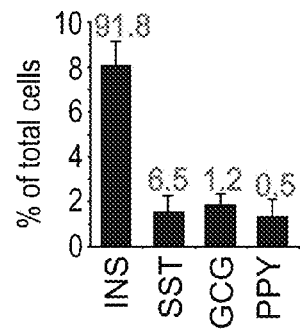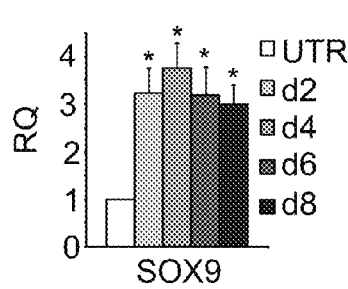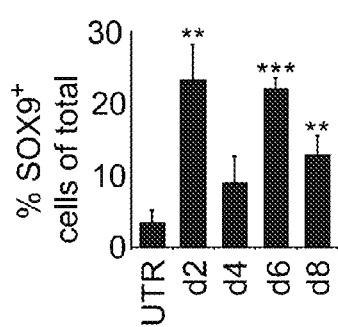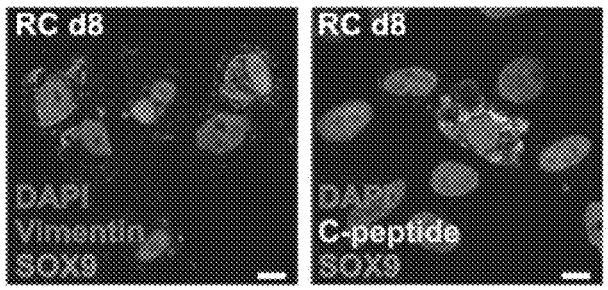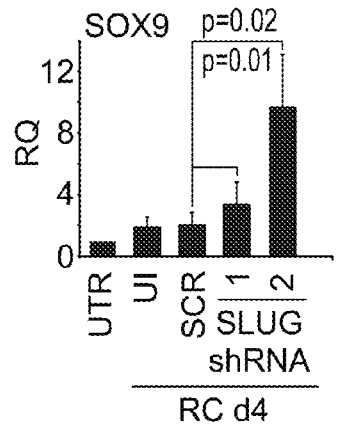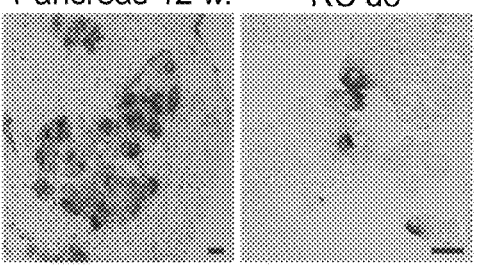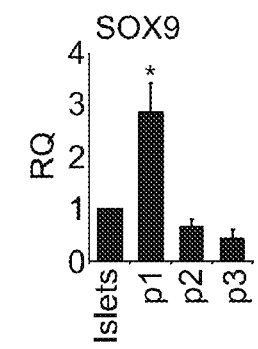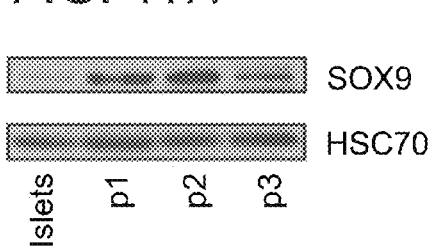

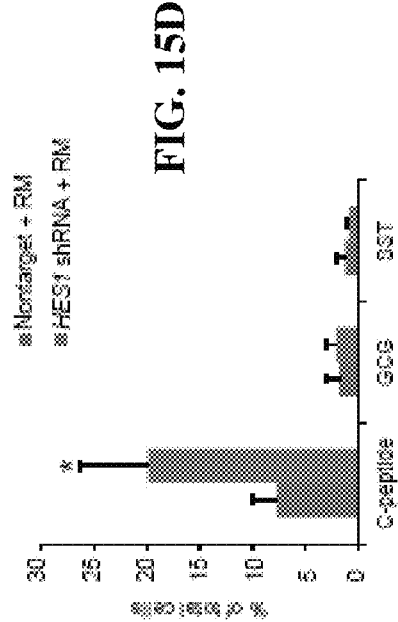
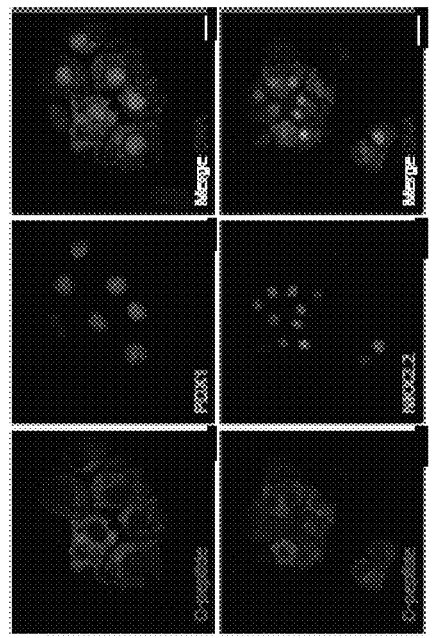
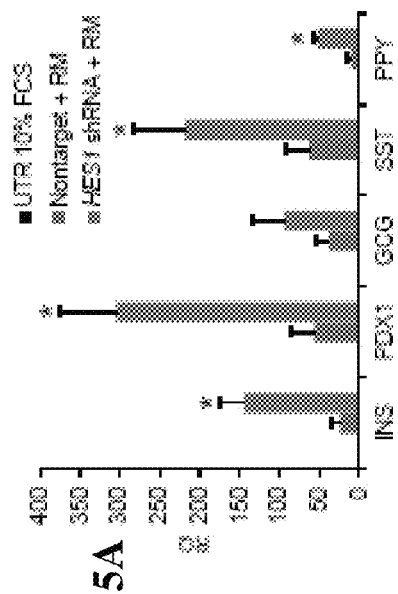
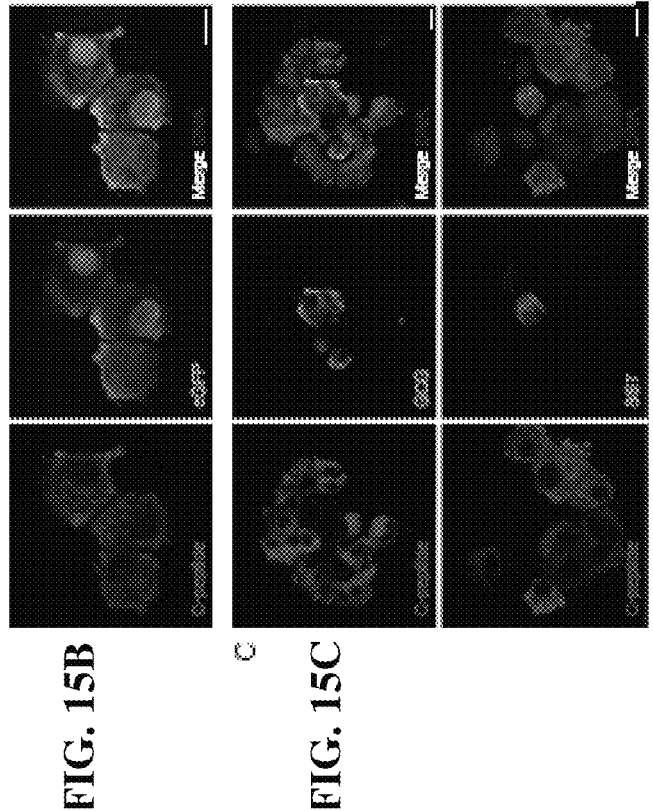
FIG. 15A  FIG. 15B  FIG. 15C  FIG. 15D  FIG. 15E

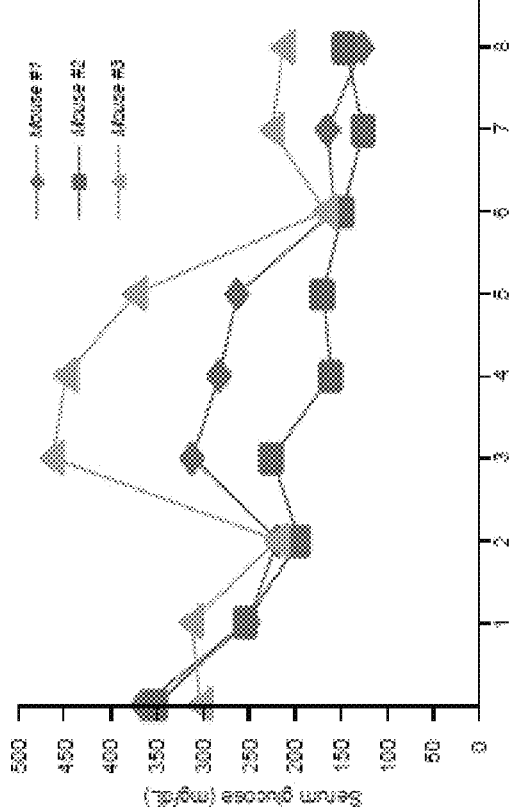
FIG. 16A
FIG. 16B
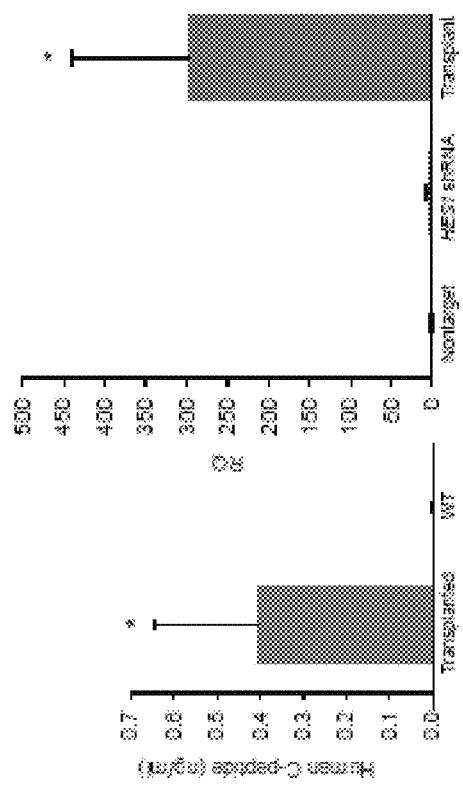
FIG. 16C

SEQUENCE LISTING

```
<160> NUMBER OF SEQ ID NOS: 57

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
agaagaggcc atcaagcaga                                                   20
```

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
caggtgttgg ttcacaaagg                                           20

<210> SEQ ID NO 3
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 3
aagctcacgc gtggaaag                                             18

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
gccgtgagat gtacttgttg aa                                        22

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 5
agcgagaagt gccaactcc                                            19

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
ttgtacaggt cccgctcttt                                           20

<210> SEQ ID NO 7
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 7
gtacaaggca gctggcaac                                            19

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

```
<400> SEQUENCE: 8
tgggaagctg agaatgatct g                                              21

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
accccagact ccgtcagttt                                                20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
acagcagctc tgccaagaag                                                20

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
tctagtgccc atttactctg gac                                            23

<210> SEQ ID NO 12
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 12
gcaggtggac aggagcag                                                  18

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
agccacatcg ctcagacac                                                 19

<210> SEQ ID NO 14
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 14
gcccaatacg accaaatcc                                                 19

<210> SEQ ID NO 15
<211> LENGTH: 23
```

```
<212> TYPE: DNA
<213> ORGANISM: Artificial sequence
<220> FEATURE:
<223> OTHER INFORMATION: Single strand DNA oligonucleotide

<400> SEQUENCE: 15
tctacaaccc tgaagtgctt gat                                              23

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
caatctgcag acagacactg g                                                21

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
agaccctcat gaaccgacag                                                  20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ggctctgtgg cttttctctc                                                  20

<210> SEQ ID NO 19
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 19
gcagatgctg gacgacag                                                    18

<210> SEQ ID NO 20
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 20
tcctgcagct ggaactctg                                                   19

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
tgtgtcacca gcatccactc                                                  20
```

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
cacttggacc tcaatggaga a                                         21

<210> SEQ ID NO 23
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 23
ttaccaaatt gtagaggctt tcg                                       23

<210> SEQ ID NO 24
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 24
ccctgcctct atacactcac tacc                                      24

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
tgatcccaca aacgagaaca                                           20

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26
tgtgattatt tgcttgcatg g                                         21

<210> SEQ ID NO 27
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 27
ctgctcagga cctactaaca acaa                                      24

<210> SEQ ID NO 28
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 28
gtccagcttg gaggacctt                                                19

<210> SEQ ID NO 29
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 29
cgagggcctt cagtactcc                                                19

<210> SEQ ID NO 30
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 30
ggggacttgg agcttgagt                                                19

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
cgttggggat gacagagagt                                               20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
cgagtcctgc ttcttcttgg                                               20

<210> SEQ ID NO 33
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 33
gctgcaggac tctaatccag a                                             21

<210> SEQ ID NO 34
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 34
atctccggag gtgggatg                                                 18

<210> SEQ ID NO 35
<211> LENGTH: 20

```
<212> TYPE: DNA
<213> ORGANISM: Artificial sequence
<220> FEATURE:
<223> OTHER INFORMATION: Single strand DNA oligonucleotide

<400> SEQUENCE: 35
tggttgcttc aaggacacat                                              20

<210> SEQ ID NO 36
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 36
gttgcagtga gggcaagaa                                               19

<210> SEQ ID NO 37
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 37
ctccatgtgc cggatagc                                                18

<210> SEQ ID NO 38
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 38
cgatttcacc agaagcctct ac                                           22

<210> SEQ ID NO 39
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 39
gccgagagct acacgttca                                               19

<210> SEQ ID NO 40
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 40
gaccggtgca atcttcaaa                                               19

<210> SEQ ID NO 41
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 41
gtacccgcac ttgcacaac                                               19
```

-continued

```
<210> SEQ ID NO 42
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 42
tcgctctcgt tcagaagtct c                                           21

<210> SEQ ID NO 43
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 43
gcaccacgtt caccagcta                                              19

<210> SEQ ID NO 44
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 44
cagcctcatg gccagttc                                               18

<210> SEQ ID NO 45
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 45
aaggcatcac tatggacttt ctct                                        24

<210> SEQ ID NO 46
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 46
gccagtttga tcccagtatt tt                                          22

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47
accccaccta aagcctgtct                                             20

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 48
aggcaaagca gtcctgagtc                                          20

<210> SEQ ID NO 49
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 49
cgctgtgttc atggtctaga aa                                       22

<210> SEQ ID NO 50
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 50
catagagagc agagattggt aggc                                     24

<210> SEQ ID NO 51
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 51
gccactacta cacgaccatc c                                        21

<210> SEQ ID NO 52
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 52
caaacttggt tcggaagtca t                                        21

<210> SEQ ID NO 53
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 53
agggagaagc agaaggaaca ag                                       22

<210> SEQ ID NO 54
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 54
cctaagagcg agttggcact g                                        21

<210> SEQ ID NO 55
<211> LENGTH: 21

```
<212> TYPE: DNA
<213> ORGANISM: Artificial sequence
<220> FEATURE:
<223> OTHER INFORMATION: HES1 siRNA target sequence

<400> SEQUENCE: 55
tggccagttt gctttcctca t                                              21

<210> SEQ ID NO 56
<211> LENGTH: 21
<212> TYPE: DNA
<213> ORGANISM: Artificial sequence
<220> FEATURE:
<223> OTHER INFORMATION: HES1 siRNA target sequence

<400> SEQUENCE: 56
ccagatcaat gccatgacct a                                              21

<210> SEQ ID NO 57
<211> LENGTH: 21
<212> TYPE: DNA
<213> ORGANISM: Artificial sequence
<220> FEATURE:
<223> OTHER INFORMATION: HES1 siRNA target sequence

<400> SEQUENCE: 57
gaaagtcatc aaagcctatt a                                              21
```

METHODS OF EXPANDING AND REDIFFERENTIATING ISLET BETA CELLS

RELATED APPLICATIONS

This application is a Continuation-In-Part (CIP) of PCT Patent Application No. PCT/IL2011/000738 having International filing date of Sep. 15, 2011, which claims the benefit of priority of U.S. Provisional Patent Application No. 61/487,782 filed on May 19, 2011, and 61/382,956 filed on Sep. 15, 2010. The contents of the above applications are all incorporated herein by reference.

FIELD AND BACKGROUND OF THE INVENTION

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors. With the development of new islet isolation and immunosuppression procedures, significant success has been reported using islets from 2-3 donors per recipient (Shapiro A M, Lakey J R, Ryan E A et al. New Engl J Med 2000; 343:230-238). This progress underscores the urgent need for developing alternatives to human pancreas donors, namely abundant sources of cultured human 13 cells for transplantation.

Terminally differentiated, postmitotic islet cells are difficult to expand in tissue culture. Adult and fetal human islet cells grown on HTB-9 matrix in RPMI 1640 medium containing 11 mM glucose, and supplemented with 10% FBS and hepatocyte growth factor, were shown to proliferate at the most for 10-15 population doublings, after which they underwent senescence. The replication span could not be extended by expression of the catalytic subunit of human telomerase (hTERT), which was introduced into the cells with a retrovirus (Halvorsen T L, Beattie G M, Lopez A D, Hayek A, Levine F. J Endocrinol 2000; 166:103-109). Due to massive cell death, this method resulted in a 3-4 expansion of the islet cell mass.

The process of beta cell expansion by prolonged culture is accompanied by dedifferenetiation of the cells.

In many instances, the dedifferentiation of cells is accompanied by drastic changes in phenotype in which their morphology changes from that of epithelial cells containing extensive cell-cell junctions and cytokeratin filament networks, to cells with a fibroblast or mensenchymal appearance. This process of dedifferentiation is known as an epithelial to mesenchymal transition (EMT) and is believed to be mediated in part by the induction of the zinc finger transcription factor Snail.

Slug, a Snail family member, has been implicated in the re-epitheliazation of cutaneous wounds, as well as in the regeneration of damaged skeletal muscle after damage. In the area of pancreatic stem cells, Gershengorn et al [Science, 2004, 306, 2261-2264], suggested that cultured primary beta cells are capable of EMT and dedifferentiation into a fibroblastoid-like cell type. Gershengorn suggested that this process could be reversed, and these fibroblastoid cells could then be redifferentiated into pancreatic endocrine cells by a so-called mesenchymal to epithelial transition. Following publication of this article, Gershongorn retracted this suggestion and showed that it is the mesenchymal stem cells present in the islets that undergo differentiation and not dedifferentiated beta cells [Davani et al., Stem cells, Volume 25, Issue 12, Pages 3215-3222, 2007].

An alternative to forced expansion of post-mitotic β cells is the induction of differentiation of stem/progenitor cells, which have a natural self-expansion capacity, into insulin-producing cells. The directed differentiation of embryonic stem cells has generated cells that only produce low amounts of insulin, compared to β cells, and their potential use in transplantation has met with ethical objections, as well as concerns regarding risk of teratomas.

Adult stem cells have also been differentiated into insulin-producing cells. However, the efficiency of expansion of these cell types in tissue culture and their rate of differentiation into insulin-producing cells need to be greatly improved to allow generation of significant cell numbers for transplantation.

It has been clearly demonstrated that committed cells can be at least partly reprogrammed with dominant genes that activate a cascade of developmental events. U.S. Publication No. 2005/0244966 to the present inventors teaches the reprogramming of fetal hepatic cells into beta-like insulin-producing cells by expression of dominant transcription factors, such as Pdx1, that direct the development of endocrine pancreas. The human fetal liver cells were induced to produce and store mature insulin in significant amounts, about a third of those produced by normal β cells, release it in response to physiological glucose levels, and replace β-cell function in STZ-diabetic nonobese-diabetic severe combined immunodeficient (NOD-scid) mice. The modified cells expressed multiple β-cell genes.

Islet cells have been expanded ex vivo in the presence of epidermal growth factor and nerve growth factor. Although these cells show high insulin content, they do not secrete insulin in response to glucose (Lechner A. et al., Biochem Biophys Res Commun 327:581-588, 2005).

International Application WO2006/054305 teaches expansion of islet cells in CMRL-1066 medium.

A number of factors have been shown to promote both β-cell proliferation and differentiation in tissue culture. Members of the growth hormone family, including placental lactogen (PL), growth hormone (GH) and prolactin (PRL), induce replication in neonatal rat islet cells. Significant mitogenic effects of hepatocyte growth factor (HGF) have been observed on human fetal and adult islets and mouse islets. In the presence of activin A or nicotinamide, HGF has been shown to stimulate β-cell differentiation in cultured fetal pancreatic islets as well as a pancreatic cell line. Glucagon-like peptide 1 (GLP-1), and its more stable analog exendin-4, have been shown to stimulate β-cell proliferation and to induce insulin gene expression in a pancreatic cell line. Members of the epidermal growth factor (EGF) family, including EGF, TGFα and betacellulin, have also been shown to stimulate β-cell proliferation and differentiation. Betacellulin is a potent mitogen for a number of cell types, including islet beta (β) cells. It was shown to increase islet neogenesis in alloxan and STZ-treated mice, and accelerate islet-regeneration in 90%-pancreatectomized rats [Li L, et al., Endocrinology 2001; 142:5379-5385].

Rukstalis et al [Endocrinology 147(6) 2997-3006] teaches that the transcription factor Snail modulates hormone expression in immortalized pancreatic endocrine cell lines. Further, it was disclosed that down-regulation of Snail in those cell lines using siRNA increased insulin gene expression.

U.S. Publication No. 2006/0292127 teaches dedifferentiating, and not redifferentiating, beta cells by contacting the cells with agents that regulate Snail/slug/slit family of transcription factors.

International Application WO2006/054305 teaches redifferentiation of expanded Beta cells in a medium comprising betacellulin and/or ngn-3.

SUMMARY OF THE INVENTION

According to an aspect of some embodiments of the present invention there is provided a method of ex-vivo increasing insulin content in adult islet beta cells comprising exposing adult islet beta cells to a culture medium comprising nicotinamide, exendin-4, activin A and glucose, the culture medium being devoid of serum, thereby increasing the insulin content in adult islet beta cells.

A method of ex-vivo increasing insulin content in progenitor cells which express SLUG, comprising downregulating an amount or activity of the SLUG in the progenitor cells, thereby increasing insulin content in the progenitor cells.

According to an aspect of some embodiments of the present invention there is provided an isolated population of cells, comprising an siRNA which down-regulates SLUG, wherein the cells secrete insulin.

According to an aspect of some embodiments of the present invention there is provided an isolated population of cells generated according to the method of the present invention.

According to an aspect of some embodiments of the present invention there is provided a method of treating diabetes in a subject, comprising transplanting a therapeutically effective amount of the population of adult islet beta cells of the present invention into the subject, thereby treating diabetes.

According to an aspect of some embodiments of the present invention there is provided a use of the population of the adult islet beta cells of the invention to treat diabetes in a subject.

According to an aspect of some embodiments of the present invention there is provided a pharmaceutical composition comprising as an active ingredient the population of adult islet beta cells of the present invention.

According to some embodiments of the invention, the method comprises:

(a) exposing the adult islet beta cells to a culture medium comprising the nicotinamide, the exendin-4, the activin A, wherein the glucose is present at a concentration of 10-100 mM; and subsequently (b) exposing the adult islet beta cells in an additional culture medium comprising the nicotinamide and the exendin-4, wherein the glucose is present at a concentration of 0.5-10 mM.

According to some embodiments of the invention, the method further comprises contacting the adult islet beta cells with an agent capable of down-regulating activity and/or expression of at least one component participating in a NOTCH pathway prior to the exposing, the component being up-regulated in B cell dedifferentiation above a predetermined threshold.

According to some embodiments of the invention, the agent is an oligonucleotide directed to an endogenous nucleic acid sequence expressing the at least one component participating in the NOTCH pathway.

According to some embodiments of the invention, the at least one component is selected from the group consisting of Hairy and Enhancer of Split 1 (HES1), NOTCH1, NOTCH 2 and NOTCH 3.

According to some embodiments of the invention, the at least one component is HES1.

According to some embodiments of the invention, the agent is an siRNA molecule as set forth in SEQ ID NO: 55, SEQ ID NO: 56 or SEQ ID NO: 57.

According to some embodiments of the invention, the nicotinamide is present at a concentration of 1-100 mM.

According to some embodiments of the invention, the exendin-4 is present at a concentration of 1-100 nM.

According to some embodiments of the invention, the activin A is present at a concentration of 1-100 nM.

According to some embodiments of the invention, the additional medium is devoid of activin A.

According to some embodiments of the invention, the culture medium is devoid of betacellulin.

According to some embodiments of the invention, the additional medium is devoid of betacellulin.

According to some embodiments of the invention, the adult islet beta cells comprise dedifferentiated adult islet beta cells.

According to some embodiments of the invention, the dedifferentiated adult islet beta cells comprise induced pluripotent stem cells generated from beta cells.

According to some embodiments of the invention, the dedifferentiated adult islet beta cells are generated by culturing the adult islet beta cells for at least 10 passages.

According to some embodiments of the invention, the culturing is effected in CMRL medium.

According to some embodiments of the invention, the method further comprises expanding the islet beta cell prior to step (a).

According to some embodiments of the invention, the step (a) is effected for 6 days.

According to some embodiments of the invention, the step (b) is effected for 2 days.

According to some embodiments of the invention, the method further comprises isolating the adult islet beta cells following step (b).

According to some embodiments of the invention, the isolating is effected using a zinc binding dye.

According to some embodiments of the invention, the zinc binding dye comprises Newport green.

According to some embodiments of the invention, the isolating is effected using anti-NCAM antibodies.

According to some embodiments of the invention, the adult islet beta cells are trypsinized.

According to some embodiments of the invention, the method further comprises contacting the adult islet beta cells with an agent which down-regulates an amount or activity of SLUG.

According to some embodiments of the invention, the progenitor cells are selected from the group consisting of dedifferentiated adult islet beta cells, mesenchymal stem cells and induced pluripotent stem cells dedifferentiated from beta cells.

According to some embodiments of the invention, the downregulating is performed using a polynucleotide agent directed against the SLUG.

According to some embodiments of the invention, the downregulating is performed using an antibody.

According to some embodiments of the invention, the polynucleotide agent comprises an siRNA agent or an shRNA agent.

According to some embodiments of the invention, the contacting is effected following the exposing.

According to some embodiments of the invention, the dedifferentiated adult islet beta cells are generated by culturing the adult islet beta cells for at least 10 passages.

According to some embodiments of the invention, the culturing is effected in CMRL medium.

According to some embodiments of the invention, the isolated population of adult islet beta cells is genetically modified to express a pharmaceutical agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B illustrate that beta-cell-derived cells can be expanded under xeno- and serum-free conditions. A: Micrographs of islet cells expanded in xeno-free (XF) or CMRL 1066 medium containing serum (CMRL) at passage 2. B: Immunofluorecence analysis of GFP-labeled beta cell derived (BCD) cells for proliferation marker Ki67.

Figure 2:
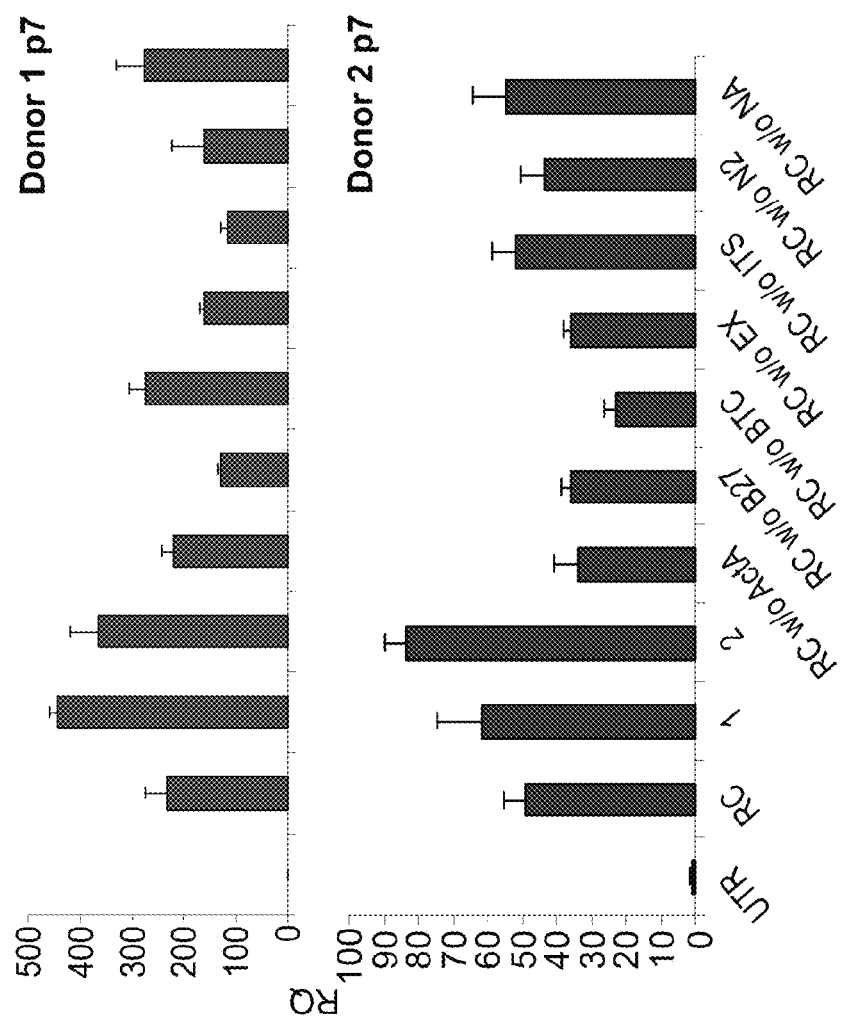

FIG. 2 illustrates the effect of different redifferentiation conditions on insulin mRNA expression. qPCR analysis of insulin transcripts in cells expanded from two donors and incubated at passage 7 for a total of 8 days under different redifferentiation conditions. The full redifferentiation cocktail (RC) comprised: CMRL 1066 medium, 25 mM glucose, antibiotics, insulin, transferrin, selenium (ITS), N2 supplement, B27 supplement, nicotinamide (NA), activin A (ActA), betacellulin (BTC), Exendin 4 (EX).
  1. Step 1: d 1-6 RC w/o BTC
  Step 2: d 7-8 RC w/o BTC, 5.6 mM glucose
  2. Step 1: d 1-6 RC w/o BTC
  Step 2: d 7-8 RC w/o BTC & ActA, 5.6 mM glucose
  Values are mean±SD, normalized to human RPLPO.

Figure 3:
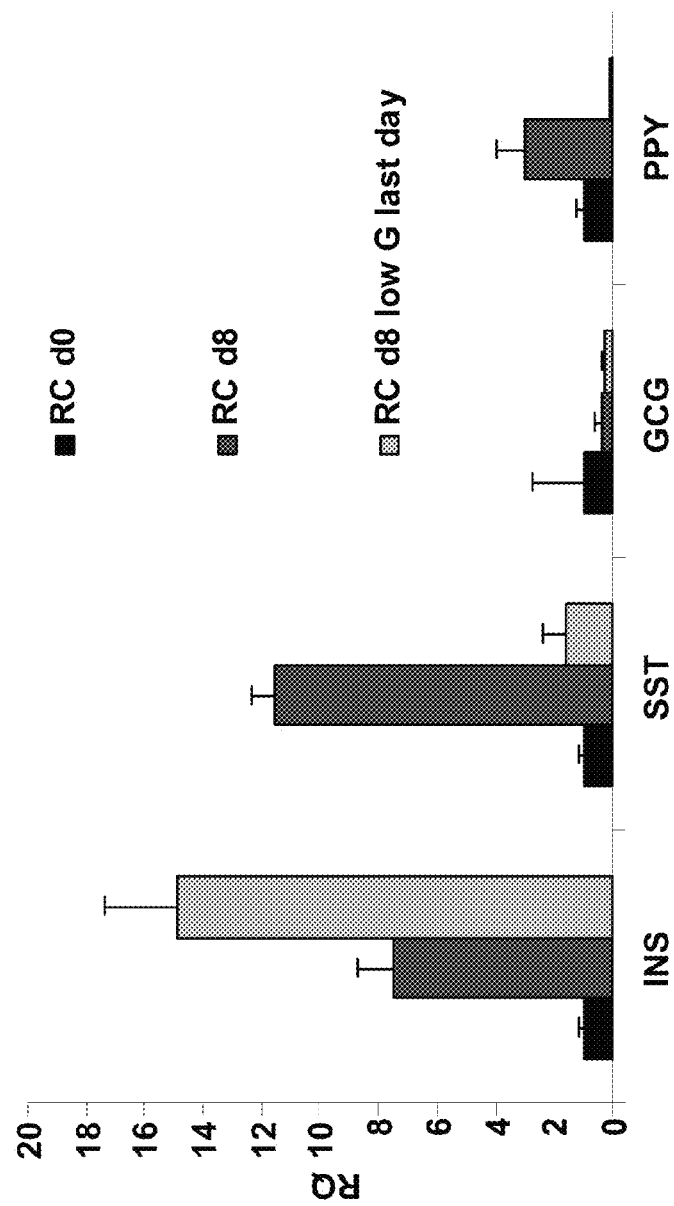

FIG. 3 illustrates that reduced glucose levels induce insulin expression, while reducing transcripts of other hormones. qPCR analysis of islets hormone transcripts in cells at passage 9 redifferentiated in RC for 8 days, or RC for 7 days and RC with 5.6 mM glucose on day 8. Values are mean±SD, normalized to human RPLPO. INS=insulin, SST=somatostatin, GCG=glucagon, PPY=pancreatic polypeptide.

Figure 4:
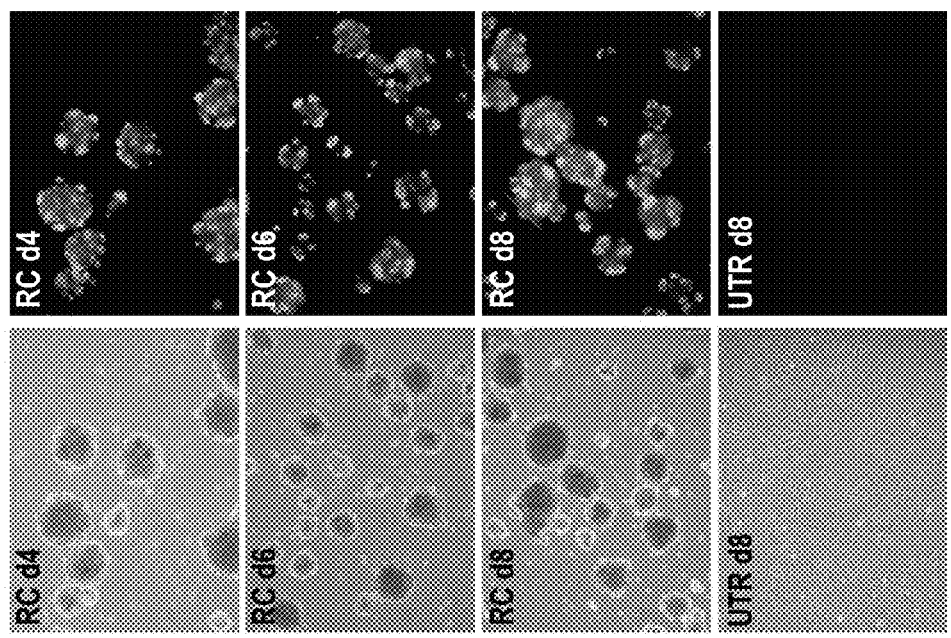

FIG. 4 are photomicrographs which visualization differentiation in live islet cells. Islet cell cultures were infected with a lentivirus expressing the fluorescence marker DsRed2 under the control of the insulin promoter. Differentiation was induced at passage 6 by transfer to RC. This resulted in cell clustering and activation of insulin promoter activity, as visualized by DsRed2 expression (right). On left are phase contrast images of the same fields. UTR, untreated.

Figure 5B:
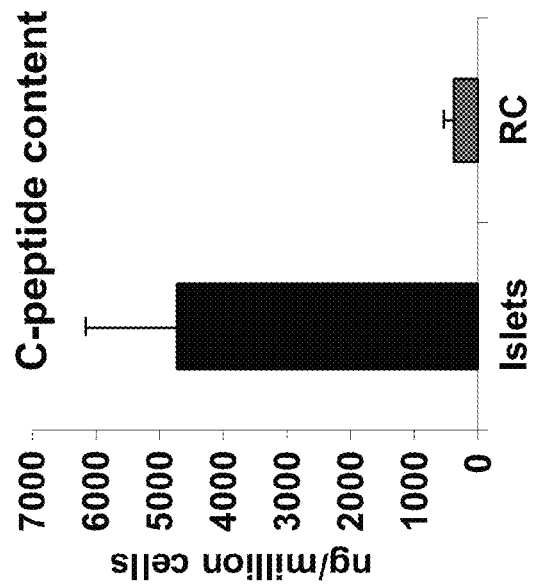
Figure 5A:
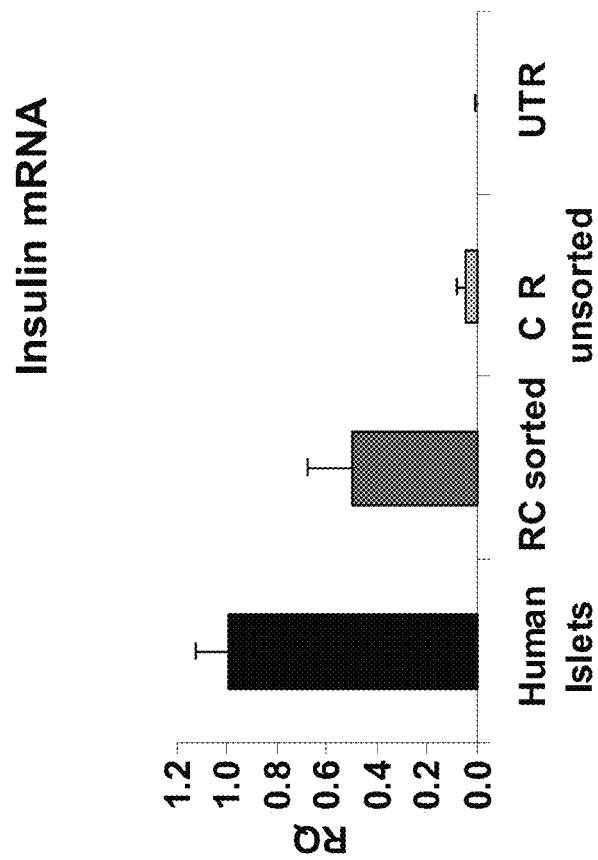

FIGS. 5A-B are graphs illustrating the effect of redifferentiation following sorting for DsRed2 expression. Expanded cells at passages 6-7 were incubated in RC for 8-11 days and sorted by FACS. A: qPCR analysis revealed upregulation of insulin expression upon redifferentiation. Values are mean±SD, normalized to human RPLPO (large ribosomal protein). B: Sorted cells contained 375 ng C-peptide per million cells, 8% of the level in human islets. UTR, untreated.

FIGS. 6A-B illustrate sorting of redifferentiated cells using Newport green (NG). A: Islet cells at passage 5 were differentiated for 8 days in RC. Insulin-containing cells were stained with NG and sorted by FACS. Dot plot of the sort shows a distinct population of fluorescent cells sorted in gate P2. B: qPCR analysis of insulin transcripts in sorted cells, unsorted differentiated cells, and untreated (UTR) cells. Values are mean±SD, normalized to human RPLPO.

FIGS. 7A-F illustrate the development of conditions for islet cell differentiation, and demonstration that differentiation represents predominantly BCD-cell redifferentiation. A: qPCR analysis of beta-cell gene expression in expanded islet cells at p6 incubated in SFM for the indicated number of days. Values are mean±SD relative to untreated cells (d0) (n=3-4 donors) and normalized to human RPLPO. *$p<0.05$; **$p<0.005$. B-D: An assay for screening islet cell differentiation conditions. Islet cells are infected with a RIP-DsRed2 lentivirus (B) followed by testing different differentiation conditions. C: No DsRed2 expression is observed in expanded cells at p5 (UTR, untreated cells), while cell transfer to SFM or RC results in insulin promoter activation, which can be monitored in live cells by appearance of DsRed2 fluorescence. Bar=200 µm. D: Flow cytometry quantitation of differentiation reveals that treatment with RC results in a 6-fold higher number of redifferentiated cells, compared with SFM. E: Schematic representation of the viral vectors used for beta-cell labeling. F: Predictions for generation of insulin-expressing cells by different cell sources within expanded islet cell populations. Initial cultures of islet cells consist of approximately half insulin-producing beta cells (purple filled circles) and half non-beta cells (open circles). The labeling efficiency of beta cells is about 50% (green filled circles). Dedifferentiated islet cells are expanded and then differentiated in SFM or RC, and the percent eGFP$^+$ cells among C-pep$^+$ cells is quantified. Redifferentiation of BCD cells is expected to result in ~50% co-staining, given the eGFP labeling efficiency. De novo differentiation of insulin-expressing cells from non-BCD cells should result in no co-staining, while occurrence of both mechanisms will result in a low percent of co-stained cells. Co-staining quantitation revealed that redifferentiation of BCD cells was the predominant source of insulin-expressing cells generated in both conditions. Percentages indicate fraction of eGFP$^+$ cells among C-pep$^+$ cells redifferentiated from expanded islet cells at p4-6 (based on counting >400 cells in each of 3 donors). A representative micrograph is shown. DNA was stained blue with DAPI. Bar=10 µm.

FIGS. 8A-E illustrate redifferentiation of BCD cells induced by soluble factors. A,B: Kinetics of induction of beta-cell genes in islet cells at p5 treated with RC. A: qPCR analysis. Values are mean±SE relative to untreated cells (d0) (n=3-4 donors) and normalized to human RPLPO or GAPDH. *$p<0.05$; **$p<0.01$. B: Immunofluorescence analysis of cells co-stained for C-peptide and PDX1. Values are mean±SE (logarithmic scale), based on counting >500 cells from each of 3 donors at each time point. *p<0.05, relative to untreated cells (d0). A representative micrograph is shown. Bar=25 μm. C,D: Analyses of beta-cell gene expression in islet cells at p5-7 treated with RC for 8 d. C: qPCR analysis. Values are mean±SE (logarithmic scale) relative to untreated cells (d0) (n=3-4 donors) and normalized to human RPLPO. *p<0.05; p<0.005; *p<0.0005. D: Immunofluorescence analysis of cells co-stained for C-peptide and the indicated protein (in green). Bar=10 μm. The percentages indicate the fraction of cells positive for each marker among C-peptide cells. Data are mean±SD, based on counting >200 cells from each of 3 donors. E: Unsupervised clustering of gene expression patterns detected in cDNA microarray analyses of uncultured islets cells from 4 donors, expanded islet cells at p5 from 4 donors (UTR), and expanded islet cells at p5 from 3 donors treated with RC.

FIGS. 9A-D illustrate insulin production and secretion in sorted redifferentiated BCD cells. Expanded islet cells (p6-7) were infected with RIP-DsRed2 virus and treated with RC for 8 d. DsRed2$^+$ cells were sorted and analyzed. A: qPCR analysis of beta-cell transcripts. Values are mean±SE, relative to human islets (n=3 donors) and normalized to human RPLPO. B: Human C-peptide content of fresh human islets and DsRed2-sorted RC-treated islet cells. Values are mean±SE (n=3 donors). Note that most of the insulin stored is processed (only 9% proinsulin). C: Glucose-induced insulin secretion from human islets and RC-treated expanded islet cells in the presence of 16.7 mM glucose and IBMX. Values are mean±SD of human C-peptide, relative to 0 mM glucose and IBMX (n=3 donors). D: Electron microscopic analysis reveals the presence of typical insulin secretory vesicles in cells at p6 treated with RC for 8 days, comparable to those seen in beta cells in isolated human islets. Bar=0.5 μm.

FIGS. 10A-H illustrate that BCD cell redifferentiation involves mesenchymal-epithelial transition (MET). A,B: Induction of SLUG expression during islet cell dedifferentiation. A: qPCR analysis of expanded islet cells at the indicated passages. Values are mean±SE relative to uncultured islets (n=4 donors) and normalized to human RPLPO. *p<0.05. B: Immunoblotting analysis of protein extracted from uncultured islets and expanded islet cells at the indicated passage number. HSC70, heat-shock cognate 70. C: Downregulation of SLUG expression during islet cell redifferentiation. qPCR analysis of expanded islet cells at p6-7 following 8 d treatment with RC. Values are mean±SE relative to untreated cells (n=4 donors) and normalized to human RPLPO. *p<0.05. D: qPCR analysis of kinetics of changes in NCAD and ECAD transcripts in expanded islet cells at p5 during 8 d treatment with RC. Values are mean±SE (logarithmic scale for ECAD) relative to untreated cells (n=4 donors) and normalized to human RPLPO or GAPDH. *p<0.05; **p<0.01. E: Immunostaining analysis of expanded islet cells at p6 following 8 d treatment with RC shows a decrease in the number of vimentin-positive cells (mean±SD, based on counting >400 cells from each of 3 donors), and mutually-exclusive expression of vimentin and C-peptide. Arrow points to a cell that may have already lost vimentin expression but has not activated yet insulin expression. Bar=10 μm. F: Co-staining for C-peptide and BrdU in expanded islet cells at p5 following 8 d treatment with RC. Percentages indicate the fraction of cells positive for BrdU among total cells, following BrdU incorporation in days 2-8 of the redifferentiation treatment. Data are mean±SD, based on counting 500 cells from each of 3 donors. Bar=20 G: Immunoblotting analysis of expanded islet cells at p5 infected with lentiviruses expressing one of two SLUG shRNAs or a scrambled (SCR) shRNA. UTR, untreated cells. H: qPCR analysis of insulin transcripts in expanded islet cells at p5 infected with lentiviruses expressing one of two SLUG shRNAs or a scrambled shRNA and treated with RC for 4 days. Values are mean±SE relative to untreated cells (n=3-6 donors) and normalized to human RPLPO or GAPDH. p-values are relative to SCR. UI, uninfected cells treated with RC.

FIGS. 11A-H illustrate that BCD cell redifferentiation involves expression of pancreas- and islet-progenitor transcription factors SOX9 and NGN3, respectively. A: RC treatment of expanded islet cells (p6) results in generation of hormone-expressing cells other than insulin. Cells were treated with RC for 8 days and stained with antibodies for the indicated hormones (insulin-producing cells were identified by staining for C-peptide). Values are mean±SE (n=4 donors), based on counting >500 cells from each donor. Values in green indicate percent of cells positive for each hormone among a total of 1736 hormone-positive eGFP$^+$ cells scored in parallel experiments with lineage-traced cells from 6 donors. B-D: SOX9 activation during redifferentiation. Islet cells at p5 were treated with RC for 8 days. B: qPCR analysis of kinetics of upregulation of SOX9. Values are mean±SE, relative to untreated cells (d0) (n=4 donors), and normalized to human RPLPO or GAPDH. *p<0.05. C: Quantitation of SOX9' cells by immunofluorescence analysis. Values are mean±SD, based on counting >500 cells from each of 3 donors at each time point. p<0.01, *p<0.001, relative to untreated cells (d0). D: Left, Immunofluorescence analysis detects cells stained for vimentin or SOX9 alone, as well as double-positive cells. Right, C-peptide and SOX9 staining is mutually exclusive. Bar=10 μm. E: qPCR analysis of SOX9 transcripts in expanded islet cells at p5 infected with lentiviruses expressing one of two SLUG shRNAs or a scrambled shRNA and treated with RC for 4 days. Values are mean±SE relative to untreated cells (n=4-6 donors) and normalized to human RPLPO or GAPDH. UI, uninfected cells treated with RC. F: NGN3 is activated during redifferentiation. In-situ hybridization analysis of NGN3 mRNA expression in human fetal pancreas cells (left panel) and expanded islet cells at p5 following 8 d treatment with RC treated islet cells (right panel). Bar=25 μm. G-H: Transient activation of SOX9 during islet cell dedifferentiation. G: qPCR analysis of expanded islet cells at the indicated passages. Values are mean±SE relative to uncultured islets (n=3 donors) and normalized to human RPLPO. *p<0.05. H: Immunoblotting analysis of protein extracted from uncultured islets and expanded islet cells at the indicated passage number.

Figure 12A:
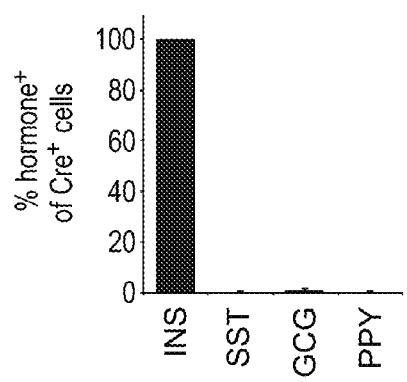
Figure 12B:
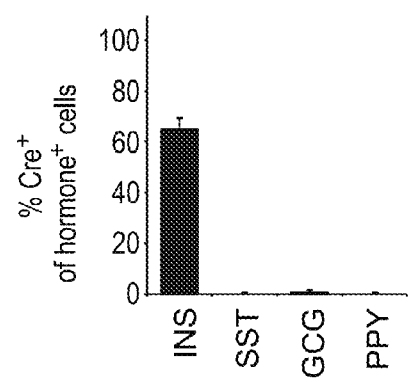

FIGS. 12A-B illustrates the pecificity of RIP-CreER transgene expression in beta cells. Human islet cells were infected with the RIP-CreER virus and co-stained for Cre protein and the 4 pancreatic islet hormones 2-3 d post infection (insulin$^+$ cells were identified by staining for C-peptide). Values are mean±SD (n=3 donors; based on counting 400 cells from each donor).

Figure 13A:
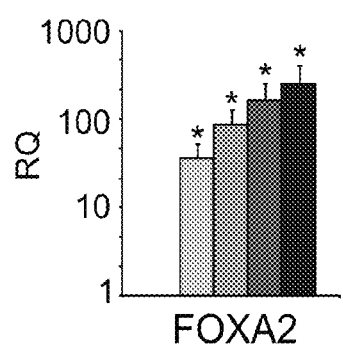
Figure 13B:
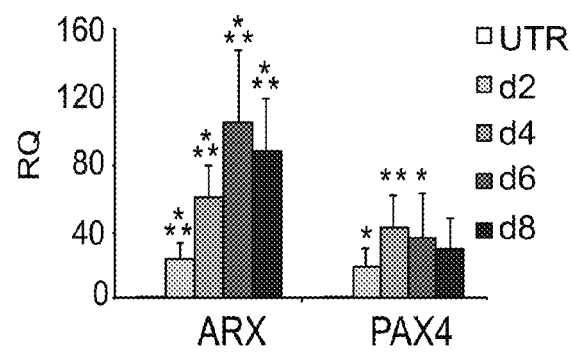

FIGS. 13A-B illustrates kinetics of upregulation of islet progenitor cell genes during RC treatment. qPCR analysis of expanded islet cells at p5 treated with RC for the indicated number of days. Values are mean±SE, relative to untreated cells (d0) (n=4 donors), and normalized to human GAPDH, *p<0.05, p<0.01, *p<0.001.

Figure 14:
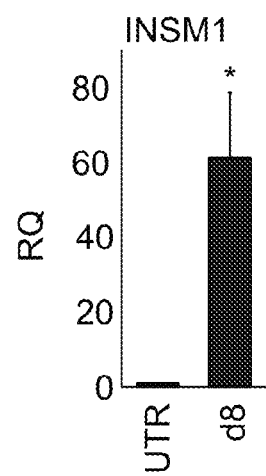

FIG. 14 illustrates upregulation of INSM1 following RC treatment. qPCR analysis of INSM1 transcripts in expanded islet cells at p5 following 8 d treatment with RC. Values are mean±SE relative to untreated cells (n=4 donors) and normalized to human RPLPO.

FIGS. 15A-E are graphs and photographs illustrating the effect of HES1 shRNA and redifferentiation medium (RM)

on redifferentiation of expanded islet cells and beta cell derived (BCD) cells. A. qPCR analysis of RNA from sorted eGFP+ cells infected at passage 5 with HES1 shRNA or nontarget viruses. Two to four days following infection cells were seeded in RM. RNA was extracted 6-11 days later and analyzed with primers for the indicated genes. RQ values are relative to untreated (UTR) cells in growth medium (10% FCS), and represent mean±SE (n=4 donors). Asterisks mark significant changes (p<0.05). B-C. Co-immunofluorescence analysis for C-peptide and the indicated antigen in islet cells infected at passage 5 with HES1 shRNA, and seeded 2 days later in RM for 4 days. Bar=10 μm. B. C-peptide/eGFP co-staining in labeled cells. C. C-peptide/islet hormone co-staining in unlabeled cells. D. Quantitation of 2000 cells in each group in the experiment shown in C. Values are mean±SE (n=3 donors). No hormone-positive cells were found in untreated cells. Asterisks mark significant changes (p<0.05). E. Co-immunofluorescence analysis for PDX1 or NKX2.2 and C-peptide in islet cells infected at passage 5 with HES1 shRNA virus. Cells were seeded in RM 2 days following infection, and stained 4 days later. Bar=10 μm (top) and 20 μm (bottom).

FIGS. 16A-D are graphs and photographs illustrating that transplantation of cells treated with HES1 shRNA into hyperglycemic immunodeficient mice corrects glycemia. NOD-SCID mice were made diabetic by STZ treatment and transplanted with $2 \times 10^6$ expanded islet cells infected at passage 5 with HES1 shRNA virus. A. Changes in blood glucose levels in each mouse. B. Serum human C-peptide levels 40 days following transplantation. Values are mean±SD (n=3 mice). C. Insulin transcript levels in RNA extracted from the transplants 56 days following transplantation, in comparison to shRNA-infected cells in vitro. RQ values are relative to non-target-infected cells in vitro, and represent mean±SE (n=3 transplants). D. Immunohistochemistry of insulin and C-peptide in transplant sections 56 days following transplantation. Dashed red lines mark transplant-kidney boundary. Bar=100 μm. Human islet sections were used as positive control (bar=40 μm).

DESCRIPTION OF SPECIFIC EMBODIMENTS OF THE INVENTION

The present invention, in some embodiments thereof, relates to a method of increasing insulin content in adult islet beta cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Thus, according to one aspect of the present invention there is provided a method of ex-vivo increasing insulin content in adult islet beta cells comprising exposing adult islet beta cells to a culture medium comprising nicotinamide, exendin-4, activin A and glucose, the culture medium being devoid of serum, thereby increasing the insulin content in adult islet beta cells.

As used herein the phrase "ex-vivo" refers to cells which are removed from a living organism and cultured outside the organism (e.g., in a test tube).

As used herein, the phrase "adult islet beta cells" refers to post-natal (e.g., non-embryonic) pancreatic islet endocrine cells which are capable of secreting insulin in response to elevated glucose concentrations and express typical beta cell markers. Examples of beta cell markers include, but are not limited to, insulin and pdx.

The isolated adult islet beta cells of this aspect of the present invention may be of homogeneous or heterogeneous nature.

Thus, for example, the adult islet beta cells of this aspect of the present invention may be comprised in isolated pancreatic islets. Islet cells may be comprised of the following: 1) beta cells that produce insulin; 2) alpha cells that produce glucagon; 3) delta cells (or D cells) that produce somatostatin; and/or F cells that produce pancreatic polypeptide. The polypeptide hormones (insulin, glucagon, somatostatin and pancreatic polypeptide) inside these cells are stored in secretary vesicles in the form of secretory granules.

Methods of isolating islets are well known in the art. For example, islets may be isolated from pancreatic tissue using collagenase and ficoll gradients. Preferably the adult islet beta cells of the present invention are dispersed into a single cell suspension—e.g. by the addition of trypsin or by trituration.

The adult islet beta cells may be further isolated being substantially free from other substances (e.g., other cells, proteins, nucleic acids, etc.) that are present in its in-vivo environment e.g. by FACs sorting.

The adult islet beta cells may be obtained from any autologous or non-autologous (i.e., allogeneic or xenogeneic) mammalian donor. For example, cells may be isolated from a human cadaver.

Dedifferentiation of the adult islet beta cells may be effected by expansion (i.e. culturing) for a prolonged number of passages—e.g. in CMRL medium.

As used herein, the term "expanding" refers to increasing the number and overall mass of adult islet beta cells of the present invention by the process of cell division, rather than simply enlarging by hypertrophy.

According to one embodiment, the cells are expanded in Mesencult XF medium comprising glucose at a concentration of about 10-100 mM glucose, more preferably 10-50 mM, more preferably 10-25 mM, such as for example 25 mM.

The cells are preferably expanded for at least 6 passages, 7 passages, 8 passages, 9 passages, 10 passages, 11 passages, 12 passages, 13 passages, 14 passages, 15 passages or at least 16 passages.

According to a particular embodiment, the expanding is effected under adherent conditions which comprise incubating on an attachment medium selected from the group consisting of laminin, fibronectin, matrigel and Mesencult XF attachment substrate.

According to another embodiment, dedifferentiation of the adult islet beta cells may be effected by transfecting the cells with genes known to generated induced pluripotent stem cells (iPS) cells. Oct-3/4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (C-myc, L-myc, and N-myc), Nanog, and LIN28, have been identified to increase the induction efficiency.

According to one embodiment, the cells are redifferentiated by:

(a) incubating adult islet beta cells in a culture medium comprising nicotinamide, exendin-4, activin A and 10-50 mM glucose, the culture medium being devoid of serum; and subsequently (b) incubating the adult islet beta cells in an additional culture medium comprising nicotinamide, exendin-4, and 0.5-10 mM glucose.

Exemplary concentration ranges of nicotinamide include 1-100 mM, more preferably 1-50 mM, more preferably 1-20 mM, such as for example 10 mM.

Exemplary concentration ranges of exendin 4 include 1-100 nM, more preferably 1-50 nM, more preferably 1-20 nM, such as for example 8 nM.

Exemplary concentration ranges of activin A include 1-100 nM, more preferably 1-50 nM, more preferably 1-20 nM, such as for example 4 nM or 8 nM.

For step A, exemplary concentration ranges of glucose include 10-100 mM, more preferably 10-50 mM, more preferably 10-25 mM, such as for example 25 mM.

For step B, exemplary concentration ranges of glucose include 0.5-10 mM, more preferably 1-10 mM, more preferably 2.5-7.5 mM, such as for example 5.6 mM.

Cells obtained using the methods described herein are capable of secreting insulin in a glucose responsive manner and typically express beta cell specific genes (e.g. PDX-1).

According to a particular embodiment, at least 10% of the cells of the isolated populations generated according to the methods described herein are cells redifferentiated from beta cells.

According to a particular embodiment, at least 20% of the cells of the isolated populations generated according to the methods described herein are cells redifferentiated from beta cells.

According to a particular embodiment, at least 30% of the cells of the isolated populations generated according to the methods described herein are cells redifferentiated from beta cells.

According to a particular embodiment, at least 40% of the cells of the isolated populations generated according to the methods described herein are cells redifferentiated from beta cells.

According to still another embodiment, at least 20% of the cells of the isolated populations generated according to the methods described herein secrete insulin.

According to still another embodiment, at least 30% of the cells of the isolated populations generated according to the methods described herein secrete insulin.

According to still another embodiment, at least 40% of the cells of the isolated populations generated according to the methods described herein secrete insulin.

According to still another embodiment, at least 50% of the cells of the isolated populations generated according to the methods described herein secrete insulin.

Preferably, a majority of the cells in the populations described herein express PDX1, NKX2.2, NKX6.1, IAPP and PC1/3 and additional proteins essential for beta cell function.

Preferably, the cells express an increase amount of beta cell transcription factors (e.g. HBLX9, NEUROD, NKX2.2, and NKX6.1), as compared to non-redifferentiated beta cells, as measured by RT-PCR.

Other genes which may be upregulated in the isolated populations described herein include KIR6.2, SUR1 and GCK.

The present inventors have shown that in order to enhance the effect of the presently described cocktail of soluble agents on the redifferentiation of the adult islet beta cells, the cells are pretreated with an agent capable of down-regulating activity and/or expression of at least one component participating in a NOTCH pathway prior to the exposing, the component being up-regulated in B cell dedifferentiation above a predetermined threshold. As illustrated in Example 3, such a combination has an unexpected synergistic effect on the amount of insulin produced and beta cell specific proteins expressed in the cells.

The phrase "component participating in the NOTCH pathway" refers to a polypeptide or polynucleotide involved in the NOTCH signaling pathway. Exemplary components are described herein below.

The Notch signaling pathway is a conserved intercellular signaling mechanism that is essential for proper embryonic development in numerous metazoan organisms.

Members of the Notch gene family (NOTCHs) encode transmembrane receptors that are critical for various cell fate decisions. Multiple ligands that activate Notch and related receptors have been identified, including Serrate and Delta in Drosophila and JAG1 (MIM.601920) in vertebrates.

Four different Notch receptors (NOTCHs: NOTCH1 to NOTCH4) and five ligands (Jagged-1 (JAG1) and -2 (JAG2) and Delta-like [DLLs]: DLL1, DLL2 and DLL4) have been characterized in mammalian cells. These transmembrane receptors and ligands are expressed in different combinations in most, if not all, cell types. The Notch pathway regulates cell fate determination of neighbouring cells through lateral inhibition, depending on their ability to express either the receptors or the ligands.

Following ligand binding, NOTCHs are activated by a series of cleavages that releases its intracellular domain (NICD). This processing requires the activity of two proteases, namely ADAM17 (tumour necrosis factor-α converting enzyme or TACE MIM.603369) and presenilin-1 (PSEN1 MIM.104311), both of which also fall under the category of a component of a NOTCH pathway.

Nuclear translocation of NICD results in transcriptional activation of genes of the HESs family (Hes/E(spl) family) and HEYs family (Hesr/Hey family) through interaction of NICD with RBPSUH (or CBF1 MIM.147183), Su(H), and Lag-1, which is also known as the recombination signal sequence-binding protein (RBP)-j (also called Suppressor of Hairless, Su(H)), each of these also falling under the category of a component of a NOTCH pathway.

Overall, when activated, Notch signalling enables neighbouring cells to acquire distinct phenotypes, through a process named lateral inhibition. The Notch receptor is pre-cleaved in the Golgi and is targeted subsequently to the plasma membrane where it interacts with ligands located on neighbouring cells. Receptor-ligand interaction results in a conformational change in the receptor, thus enabling additional cleavages by TACE and the γ-secretase complex. This proteolytic activity enables the Notch intracellular domain (NICD) to translocate to the nucleus where it activates the transcription of target genes (e.g. the Hes and Hey family of transcriptional repressors).

Monoubiquitylation (Ub) of the ligand by mindbomb (MIB) induces endocytosis of the ligand and the Notch extracellular domain (NECD) into the ligand cells where additional signalling might be initiated.

Notch receptors undergo a complex set of proteolytic processing events in response to ligand activating, which eventually leads to release of the intracellular domain of the receptor. Signal transduction is normally initiated by binding to transmembrane ligands of the Serrate or Delta class, which induces proteolytic release of the intracellular NOTCH domain (NICD).

Free NICD translocates to the nucleus to form a short-lived complex with a Rel-like transcription factor, CSL, and Mastermind-like co-activators that activates lineage-specific programs of gene expression.

As mentioned, the present invention contemplates downregulating any component of the NOTCH pathway that is up-regulated in B cell dedifferentiation above a predetermined threshold.

Methods of analyzing whether a particular component is upregulated during B cell differentiation are known in the art, and may be effected on the RNA level (using techniques such as Northern blot analysis, RT-PCR and oligonucleotides microarray) and/or the protein level (using techniques such as ELISA, Western blot analysis, immunohistochemistry and the like, which may be effected using antibodies specific to the NOTCH pathway component).

According to one embodiment the NOTCH pathway component is upregulated by at least 1.5 times, more preferably by at least 2 times and more preferably by at least 3 times.

According to another embodiment, the NOTCH pathway component is Hairy and Enhancer of Split 1 (HES1; NM_005524, NP_005515), NOTCH1 (NM_017617, NP_060087.3) NOTCH 2 (NM_024408, NP_077719.2) and NOTCH 3 (NM_000435, NP_000426.2).

Downregulation of NOTCH pathway components can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

The present inventors have shown that the redifferentiation protocol described above causes a down-regulation of a gene named SLUG (snail homolog 2, encoding the protein having a Swiss prot number 043623)—GenBank™ accession number BC014890.

It will be appreciated that the present invention contemplates for this redifferentiation protocol (or any additional redifferentiation protocol) additional ways of downregulating SLUG (e.g. by using agents which are directed specifically against this protein such as by using antibodies or siRNA agents).

Following is a list of agents capable of downregulating expression level and/or activity of SLUG or a component of the NOTCH pathway.

One example, of an agent capable of downregulating SLUG or a component of the NOTCH pathway is an antibody or antibody fragment capable of specifically binding thereto. Preferably, the antibody specifically binds at least one epitope of a SLUG or a component of the NOTCH pathway. As used herein, the term "epitope" refers to any antigenic determinant on an antigen to which the paratope of an antibody binds.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Downregulation of SLUG or a component of the NOTCH pathway can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., SLUG or a component of the NOTCH pathway) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573: 127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Examples of suitable siRNA capable of downregulating HES1 can be the siRNA of SEQ ID NO: 55 (TGGCCAGTTTGCTTTCCTCAT), of SEQ ID NO: 56 (CCAGATCAATGCCATGACCTA) or SEQ ID NO: 57 (GAAAGTCATCAAAGCCTATTA).

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with some embodiments of the invention can be effected as follows. First, the selected mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a "cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, plsl, TAT(48-60), pVEC, MTS, and MAP.

Another agent capable of downregulating SLUG or a member of the NOTCH pathway is a DNAzyme molecule capable of specifically cleaving an mRNA transcript or DNA sequence of the SLUG. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 2002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of SLUG or a member of the NOTCH pathway can also be effected by using an antisense polynucleotide capable of specifically hybridizing with an mRNA transcript encoding SLUG.

Another agent capable of downregulating SLUG or a member of the NOTCH pathway is a ribozyme molecule capable of specifically cleaving an mRNA transcript encoding SLUG. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of SLUG gene in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3'--A | G | G | T |
|--------|-------|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the SLUG regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Publication Nos. 2003/017068 and 2003/0096980 to Froehler et al, and 2002/0128218 and 2002/0123476 to Emanuele et al, and U.S. Pat. No. 5,721,138 to Lawn.

Another agent capable of downregulating SLUG would be any molecule which binds to and/or cleaves SLUG. Such molecules can be SLUG antagonists, or SLUG inhibitory peptide.

It will be appreciated that a non-functional analogue of at least a catalytic or binding portion of SLUG can be also used as an agent which downregulates SLUG.

Another agent which can be used along with some embodiments of the invention to downregulate SLUG is a molecule which prevents SLUG activation or DNA binding.

The population of adult islet beta cells of the present invention may be further modified (e.g. genetic modification) to express a pharmaceutical agent such as a therapeutic agent, a telomerase gene, an agent that reduces immune mediated rejection or a marker gene. It is contemplated that therapeutic agents such as antimetabolites (e.g., purine analogs, pyrimidine analogs), enzyme inhibitors and peptidomimetics may be generally useful in the present invention. An example of a gene that may reduce immune mediated rejection is the uteroglobin gene. Uteroglobin is a protein expressed during pregnancy that confers immunologic tolerance and prevents inflammatory reactions. Methods of genetically modifying the adult islet beta cells of the present invention are described hereinabove.

According to one embodiment, following redifferentiation the beta cells are isolated from other pancreatic cells present in the islet. This may be effected using zinc binding dyes such as Newport green (see Parnaud G, et al. Proliferation of sorted human and rat beta cells. Diabetologia 2008. 51:91-100) or with anti-NCAM antibodies (see Banerjee M, Otonkoski T. A simple two-step protocol for the purification of human pancreatic beta cells. *Diabetologia* 2009. 52:621-625.).

Since the adult islet pancreatic cells of the present invention store and secrete insulin in a glucose responsive manner, they may be used for treating a disease which is associated with insulin deficiency such as diabetes.

Thus, according to another aspect of the present invention there is provided a method of treating diabetes in a subject, the method comprising transplanting a therapeutically effective amount of the population of ex-vivo expanded and re-differentiated adult islet beta cells of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the redifferentiated adult islet beta cells of the present invention, using any suitable route. Typically, beta cell therapy is effected by injection using a catheter into the portal vein of the liver, although other methods of administration are envisaged.

As mentioned hereinabove, the adult islet beta cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycin-namylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The adult islet beta cells of the present invention may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the adult islet beta cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as further detailed above.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Expanded Beta Cells as a Source of Insulin

Materials and Methods

Expansion in Xeno-Free Conditions:

Adult human islet cells were plated in plates coated with MesenCult XF attachment substrate (Stem Cell Technology, Canada) and expanded in MesenCult XF medium (Stem Cell Technology, Canada).

Redifferentiation in a Soluble Factor Cocktail:

The redifferentiation protocol was based on cell clustering in serum-free medium (SFM) in ultra low-attachment plates, and exposure to a cocktail of soluble factors in 2 steps:

Step 1:

6-day incubation in CMRL 1066 medium containing 25 mM glucose and supplemented with 1% BSA fraction V, 100 U/ml penicillin, 100 µg/ml streptomycin, ITS (insulin, transferrin, selenium), N2 supplement, B27 supplement, 10 mM nicotinamide, 8 nM exendin-4, and 8 nM activin A.

Step 2:

2-day incubation in CMRL 1066 medium containing 5.6 mM glucose and supplemented with 1% BSA fraction V, 100 U/ml penicillin, 100 µg/ml streptomycin, ITS, N2 supplement, B27 supplement, 10 mM nicotinamide, and 8 nM exendin-4.

Newport Green (NG):

Redifferentiated cells were trypsinized into a single-cell suspension, incubated in 2.5 µM NG for 10 minutes with 0.00125% Pluronic F-127 in PBS, and subjected to FACS analysis.

Results

The cells were induced to replicate at a rate comparable to that of cells growing in the presence of serum (FIG. 1A). Lineage traced beta-cell-derived (BCD) cells were shown to replicate under these conditions, as judged by Ki67 staining (FIG. 1B).

The redifferentiation protocol resulted in maximal levels of insulin mRNA, compared with all other combinations tested (FIG. 2). These levels were more than 4-fold higher, compared with some of the combinations. The reduction of glucose concentration in Step 2 resulted not only in higher insulin mRNA levels, but also in lower levels of mRNA for other islet hormones (FIG. 3). Using our lineage-tracing approach the present inventors have shown that this treatment results in specific redifferentiation of BCD cells, as opposed to cells derived from other cell types present in the islet preparations. In cells obtained from 4 different human donors the percent of C-peptide-positive cells following redifferentiation was 9.1±3.5%. Since beta cells account for about 40% (43±3%) of the primary islet-cell population, and the fraction of BCD cells remains stable during expansion, the percent of C-peptide-positive cells represents about 23% redifferentiation among BCD cells.

A reporter RIP-DsRed2 lentivirus was used in order to allow optimization of the redifferentiation protocol by following the appearance of red fluorescence in live cells (FIG. 4). This labeling method also allowed sorting of redifferentiated insulin-positive cells at the end of Step 2. The DsRed2-positive cells contained 52% of the insulin mRNA levels found in human islets (FIG. 5A). The human C-peptide content was 374±160 ng/$10^6$ cells, representing 8% of the level in human islets (FIG. 5B). The proinsulin content was 171±22 ng/$10^6$ cells, indicating that 85.6% of the proinsulin was processed to mature insulin.

The redifferentiation protocol worked reproducibly with cells from all the donors. The latest passage so far shown to respond to this treatment was passage 12, which represents a 4096-fold expansion.

Newport green (NG), a fluorescent dye known to bind to $Zn^{++}$ ions, was used to label beta cells, which contain $Zn^{++}$ ions in the insulin vesicles. This dye has been shown to be fully compatible with cell viability and function. As seen in FIG. 6A, the labeled cells can be easily distinguished from non-labeled cells and sorted by FACS. Sorting results in a great enrichment of insulin-positive cells (FIG. 6B).

Example 2

Development of Conditions for BCD Cell Redifferentiation

Materials and Methods

Cell Culture:

Human islets were received 2.8±1.2 days following isolation. Islet purity was 83±9%, as determined by staining with dithizone. Islets from individual donors (see donor list in Table 1) were dissociated into single cells, and beta cells were labelled and expanded as previously described (1-4) in CMRL 1066 medium containing 5.6 mM glucose (tissue culture reagents were from Biological Industries, Israel, unless indicated otherwise) and supplemented with 10% FCS, penicillin (50 units/ml), and streptomycin (50 µg/ml) (both from Gibco-Invitrogen).

TABLE 1

| Donor No. | Donor Sex | Donor Age (y) | Donor BMI | Islet purity (%) |
|---|---|---|---|---|
| 1 | F | 27 | ND | 95 |
| 2 | F | 63 | 39.3 | 80 |
| 3 | F | 66 | 29.4 | 83 |
| 4 | M | 50 | 37.0 | 92 |
| 5 | F | 34 | 22.5 | 80 |
| 6 | M | 42 | 22.5 | 70 |
| 7 | F | 24 | 30.9 | 90 |
| 8 | M | 57 | 34.3 | 75 |
| 9 | M | 69 | 30.4 | 85 |
| 10 | M | 45 | 31.6 | ND |
| 11 | M | 54 | 26.9 | 85 |
| 12 | M | 47 | 23.0 | 85 |
| 13 | F | 51 | 39.3 | 80 |
| 14 | M | ND | 35.0 | 80 |
| 15 | F | 36 | 43.0 | 90 |
| 16 | M | 26 | 19.8 | 65 |
| 17 | M | 57 | 32.4 | 80 |
| 18 | F | 69 | 29.7 | 90 |
| 19 | M | 29 | 20.7 | 80 |
| 20 | M | 38 | 22.9 | 85 |
| 21 | M | 58 | 33.4 | 65 |
| 22 | F | 55 | 26.6 | 80 |
| 23 | M | 55 | 22.4 | 70 |
| 24 | F | 38 | 24.0 | 75 |
| 25 | M | 55 | 27.0 | 70 |
| 26 | M | 62 | 24.2 | 90 |
| 27 | F | 38 | 20.8 | 95 |
| 28 | M | 62 | 30.6 | ND |
| 29 | F | 44 | 21.5 | 85 |
| 30 | M | 40 | 29.0 | 95 |
| 31 | F | 47 | 33.2 | 70 |
| 32 | F | 50 | 42.3 | 85 |
| 33 | M | 21 | 33.8 | 85 |
| 34 | M | 62 | 31.8 | 99 |
| 35 | M | 44 | 24.7 | 99 |
| 36 | M | 27 | 19.0 | 85 |
| 37 | M | 55 | 22.4 | 70 |
| 38 | F | 38 | 24.0 | 75 |

TABLE 1-continued

| Donor No. | Donor Sex | Donor Age (y) | Donor BMI | Islet purity (%) |
|---|---|---|---|---|
| 39 | F | 62 | 27.1 | 95 |
| 40 | M | 59 | 23.0 | 85 |
| 41 | M | 22 | 19.8 | 80 |
| 42 | M | 39 | 27.4 | 98 |
| Average ± SD | | 47 ± 14 | 28 ± 6 | 83 ± 9 |

5 µg/ml amphotericine B was added for the first ten days of culture. Cells were split 1:2 once a week. For differentiation experiments, adherent expanded islet cells were washed with PBS and trypsinzed. Cell suspension was washed with PBS, resuspended in the indicated medium, and seeded at $3.2 \times 10^4$ cells per cm$^2$ in ultra-low attachment plates (Corning). Serum free medium (SFM) consisted of CMRL 1066 containing 5.6 mM glucose and supplemented with 1% BSA fraction V (Sigma), 1×ITS (Gibco-Invitrogen), penicillin (50 units/ml), and streptomycin (50 µg/ml). Redifferentiation Cocktail (RC) medium consisted of SFM supplemented with D-glucose (final concentration 25 mM), 1×N2 supplement, 1×B27 supplement (both from Stem Cell Technologies), 10 mM nicotinamide (Sigma), 8 nM exendin-4 (Acris), and 8 nM activin A (Peprotech). Differentiation medium was changed at least every 48 hours. Primary human fibroblasts were maintained in DMEM containing 10% FCS (Gibco), 100 U/ml penicillin and 100 µg/ml streptomycin. Human bone marrow-derived mesenchymal stem cells (BM-MSC) were isolated and cultured as described (5).

Virus Production and Cell Infection:

The RIP-Cre/ER and pTrip-loxP-NEO-STOP-loxP-eGFP lentivirus vectors have been described (4). SLUG shRNAs (accession numbers TRCN-15389, -15388, -15390, -15391, -15392), and a non-target shRNA, all cloned in the pLKO.1 lentiviral vector, containing a puromycin-resistance gene, were obtained from the RNAi Consortium (Sigma-Aldrich). Virus particles were produced as previously described (4). Briefly, lentiviral vector plasmids were cotransfected with the pCMVdR8.91 and pMD2.G plasmids into 293T cells, and culture medium was harvested every 24 hours for 3 days. Cells were infected overnight in the presence of 8 µg/ml polybrene (Sigma-Aldrich). For SLUG inhibition experiments, infected cells were selected for puromycin resistance (1 µg/ml) for 3 days.

Cell Sorting:

Labeled cells were sorted using a FACS Aria cell sorter (Becton Dickinson, San Jose, Calif.) as described (2,4).

Flow Cytometry:

Adherent cells and floating cell clusters were washed with PBS and dissociated by trypsin treatment for 5-10 min at 37° C. Cells were resuspended in PBS containing 2% FCS and filtered through a cell strainer. Flow cytometry was preformed on FACsort (BD Bioscience) using FlowJo software (Tree Star). Final analysis was done using Cyflogic software (Cyflogic). Untreated cells, and infected cells without differentiation treatment, served as controls in all experiments.

Cell Proliferation and Apoptosis Analyses:

For BrdU incorporation, cells were incubated with 10 µM BrdU (Sigma) for 7 days, starting one day following initiation of RC treatment. DNA fragmentation of apoptotic cells was detected by TUNEL staining using the TACS•XL Apoptosis Detection Kit (R&D Systems Inc., Minneapolis, Minn.), according to the manufacturer's instructions.

qPCR Analyses:

Total RNA was extracted using RNAeasy Plus Micro Kit (Qiagen) according to the manufacturer's instructions or using Trizol (Sigma-Aldrich) and treated with DNA-free (Ambion) to remove genomic DNA. cDNA was prepared using High Capacity cDNA RT Kit (Applied Biosystems). qPCR was carried out in duplicates or triplicates using TaqMan Universal PCR Master Mix (Applied Biosystems) or Universal Probe Library Master Mix (Roche) in 7300 Real-time PCR System (Applied Biosystems). The results were normalized to glyceraldehyde-3-phosphate dehydrogenase (GAPDH) and/or human large ribosomal protein (RPLPO) transcripts. Primer sequences are listed in Table 2.

TABLE 2

| Gene | Sense primer | Antisense primer |
|---|---|---|
| INS | Taqman probe Hs_00355773_m1 agaagaggccatcaagcaga (SEQ ID NO: 1) | Taqman probe Hs_00355773_m1 caggtgttggttcacaaagg (SEQ ID NO: 2) |
| PDX1 | Taqman probe Hs_00426216_m1 aagctcacgcgtggaaag (SEQ ID NO: 3) | Taqman probe Hs_00426216_m1 gccgtgagatgtacttgttgaa (SEQ ID NO: 4) |
| FOXA2 | Taqman probe Hs_00232764_m1 | Taqman probe Hs_00232764_m1 |
| MAFA | Taqman probe Hs01651425_s1 agcgagaagtgccaactcc (SEQ ID NO: 5) | Taqman probe Hs01651425_s1 ttgtacaggtcccgctcttt (SEQ ID NO: 6) |
| GCG | Taqman probe Hs01031536_m1 gtacaaggcagctggcaac (SEQ ID NO: 7) | Taqman probe Hs01031536_m1 tgggaagctgagaatgatctg (SEQ ID NO: 8) |
| SST | Taqman probe Hs00174949_m1 accccagactccgtcagttt (SEQ ID NO: 9) | Taqman probe Hs00174949_m1 acagcagctctgccaagaag (SEQ ID NO: 10) |
| PPY | Taqman probe Hs00237001_m1 tctagtgcccatttactctggac (SEQ ID NO: 11) | Taqman probe Hs00237001_m1 gcaggtggacaggagcag (SEQ ID NO: 12) |
| AMY2A | Taqman probe Hs00420710_g1 | Taqman probe Hs00420710_g1 |

TABLE 2-continued

| Gene | Sense primer | Antisense primer |
|---|---|---|
| GAPDH (h) | Taqman probe Hs_99999905_m1 agccacatcgctcagacac (SEQ ID NO: 13) | Taqman probe Hs_99999905_m1 gcccaatacgaccaaatcc (SEQ ID NO: 14) |
| RPLPO | Taqman probe Hs_99999902_m1 tctacaaccctgaagtgcttgat (SEQ ID NO: 15) | Taqman probe Hs_99999902_m1 caatctgcagacagacactgg (SEQ ID NO: 16) |
| SUR1 | agaccctcatgaaccgacag (SEQ ID NO: 17) | ggctctgtggcttttctctc (SEQ ID NO: 18) |
| GCK | gcagatgctggacgacag (SEQ ID NO: 19) | tcctgcagctggaactctg (SEQ ID NO: 20) |
| KIR6.2 | tgtgtcaccagcatccactc (SEQ ID NO: 21) | cacttggacctcaatggagaa (SEQ ID NO: 22) |
| IAPP | ttaccaaattgtagaggctttcg (SEQ ID NO: 23) | ccctgcctctatacactcactacc (SEQ ID NO: 24) |
| PC1/3 | Tgatcccacaaacgagaaca (SEQ ID NO: 25) | Tgtgattatttgcttgcatgg (SEQ ID NO: 26) |
| HLXB9 | Taqman probe Hs00907365_m1 | Taqman probe Hs00907365_m1 |
| NEUROD1 | ctgctcaggacctactaacaacaa (SEQ ID NO: 27) | gtccagcttggaggacctt (SEQ ID NO: 28) |
| NKX2-2 | cgagggccttcagtactcc (SEQ ID NO: 29) | ggggacttggagcttgagt (SEQ ID NO: 30) |
| NKX6-1 | Taqman probe Hs00232355_m1 cgttggggatgacagagagt (SEQ ID NO: 31) | Taqman probe Hs00232355_m1 cgagtcctgcttcttcttgg (SEQ ID NO: 32) |
| SNAI1 | gctgcaggactctaatccaga (SEQ ID NO: 33) | atctccggaggtgggatg (SEQ ID NO: 34) |
| SNAI2 | tggttgcttcaaggacacat (SEQ ID NO: 35) | gttgcagtgagggcaagaa (SEQ ID NO: 36) |
| NCAD | Ctccatgtgccggatagc (SEQ ID NO: 37) | Cgatttcaccagaagcctctac (SEQ ID NO: 38) |
| ECAD | Gccgagagctacacgttca (SEQ ID NO: 39) | Gaccggtgcaatcttcaaa (SEQ ID NO: 40) |
| SOX9 | Gtacccgcacttgcacaac (SEQ ID NO: 41) | Tcgctctcgttcagaagtctc (SEQ ID NO: 42) |
| PTF1A | Taqman probe Hs_00603586_g1 | Taqman probe Hs_00603586_g1 |
| ARX | Gcaccacgttcaccagcta (SEQ ID NO: 43) | Cagcctcatggccagttc (SEQ ID NO: 44) |
| TCF2 | Taqman probe Hs_00172123_m1 | Taqman probe Hs_00172123_m1 |
| TWIST | Aaggcatcactatggactttctct (SEQ ID NO: 45) | Gccagtttgatcccagtatttt (SEQ ID NO: 46) |
| PAX4 | Accccacctaaagcctgtct (SEQ ID NO: 47) | Aggcaaagcagtcctgagtc (SEQ ID NO: 48) |
| INSM1 | Cgctgtgttcatggtctagaaa (SEQ ID NO: 49) | Catagagagcagagattggtaggc (SEQ ID NO: 50) |
| KRT19 | Gccactactacacgaccatcc (SEQ ID NO: 51) | Caaacttggttcggaagtcat (SEQ ID NO: 52) |

All reactions were performed with annealing at 60° C. for 40 cycles. For undetectable transcripts, the cycle number was set to 40 for comparisons.

DNA Microarray Analysis:

Total RNA was isolated using Trizol (Sigma-Aldrich) and treated with DNA-free (Ambion) to remove genomic DNA, according to the manufacturer's protocols. Hybridization to the GeneChip Human Gene 1.0 ST Arrays (Affymetrix), washing and scanning were performed according to the manufacturer's protocol. Data were normalized with the multi-average method. Batch effect removal was applied for the different samples, followed by one-way ANOVA. Clustering analysis was performed by Partek Genomics Suite software with Pearson's dissimilarity correlation and average linkage methods.

Transmission Electron Microscopy:

Cells were fixed in 2.5% glutaraldehyde (EMS) in PBS overnight at 4° C. Following several washes in PBS, the cells were postfixed in 1% OsO4 (EMS) in PBS for 2 hours at 4° C. Dehydration was carried out in graded ethanol solutions, followed by embedding in Glycid ether. Thin sections were mounted on Formvar/Carbon coated grids and examined in Jeol 1200EX transmission electron microscope. Images were captured using SIS Megaview III camera and iTEM imaging platform (Olympus).

Immunofluorescence Analyses:

Attached cells or cell clusters were trypsinzed and spotted on slides using a Shandon Cytospin4 centrifuge (Thermo Scientific). Spotted cells were fixed for 15 min at RT in 4% PFA. Paraffin sections of human pancreas were rehydrated, and antigen retrieval was preformed before staining. For BrdU staining, slides were incubated in 1.5 M HCl for 20 minutes, followed by 0.1 M sodium borate (pH 8.5) for 10 minutes at RT and 3 washes in PBS. All samples were blocked for >10 min in blocking buffer consisting of 1% BSA, 5% FGS, and 0.2% saponin. Primary antibodies were diluted in blocking buffer, and samples were incubated for either 1 hour at RT or overnight at 4° C. Slides were then washed in PBST and incubated for 40 minutes with the appropriate secondary antibody conjugated to Alexa fluorophores (all from Invitrogen, 1:1000). Images were taken using a Leica SP5 confocal microscope. Images of fluorescent living cells were taken with a Nikon microscope equipped with a NIS Elements camera and software. Expression of eGFP was detected using mouse anti-GFP (Chemicon, 1:500) or rabbit anti-GFP (Invitrogen, 1:1000). DsRed2 was visualized by endogenous fluorescence. Other primary antibodies used: mouse anti-human C-peptide (Biodesign, 1:200), rabbit anti-human C-peptide to (Abcam, 1:100), rat anti-human C-peptide (BCBC, 1:1000), mouse anti-glucagon (Sigma, 1:2000), rabbit anti-somatostatin (Dako, 1:400), rabbit anti-pancreatic polypeptide (Dako, 1:200), rabbit anti-human Ki67 (Zymed, 1:50), mouse anti-vimentin (Calbiochem, 1:50), rabbit anti-human PDX1 (Abcam, 1:500), mouse anti-prohormone convertase 1/3 (Milipore, 1:100), mouse anti-IAPP (Thermo Scientific, 1:30), mouse anti-NKX2.2 (Hybridoma Bank 74.5A5, 1:1000), mouse anti-NKX6.1 (gift from P. Serup, 1:1000), rabbit anti-SOX9 (Chemicon, 1:200), rabbit anti-FOXA2 (Abcam, 1:1000), and mouse anti-BrdU (Chemicon, 1:100). DNA was stained with DAPI (Sigma).

Immunoblotting:

Total protein was extracted by incubating cells for 10 minutes in 1% NP40 containing a protease inhibitor cocktail. Protein concentration was determined using the BCA Protein Assay Kit (Pierce). 20 μg protein were resolved on a SDS-PAGE gel. The gel was electroblotted onto Immobilon-P Transfer Membrane (Milipore), followed by incubation with rabbit anti-SOX9 (Chemicon, 1:200) or mouse anti-SLUG (Sigma, 1:50). Mouse anti-actin (Sigma, 1:2000) or mouse anti-HSC70 (SantaCruz, 1:1000) was used to monitor gel loading. The bound antibody was visualized with the appropriate horseradish peroxidase-conjugated anti-IgG and SuperSignal West Pico Chemiluminescent Substrate (Pierce). Quantification was done using TINA software.

In Situ Hybridization:

In situ hybridization analysis was performed on dewaxed paraffin sections of fetal pancreas and frozen sections of cell clusters as described (6). Cell clusters were washed once with PBS and fixed overnight in 4% PFA in PBS at 4° C. Clusters were then washed 3 times with PBS and transferred to 30% sucrose in PBS for 48 hours at 4° C. Clusters were embedded in OCT and snap-frozen. Nine-μm sections were cut using a CM3050S cryostat (Leica) and dried overnight at RT. A 557-bp fragment from the first exon of NGN3 was amplified from human genomic DNA using the primers 5'-agggagaagca-gaaggaacaag-3' (SEQ ID NO: 53) and 5'-cctaagagcgagttg-gcactg-3' (SEQ ID NO: 54). The PCR product was cloned into pMEG-T Easy Vector system (Promega), and sense/antisense probes were generated and labeled with digoxigenin using Sp6 or T7 polymerases. Hybridization was performed overnight at 55° C. with digoxigenin-labeled probes (3 μg/ml). The slides were then treated with RNaseA, washed, blocked with 10% normal goat serum (NGS) and incubated with sheep anti-digoxigenin Fab fragments conjugated to alkaline phosphatase (1:2500, Roche) in PBS containing 0.1% Tween20 (PBST, Sigma-Alrich) and 1% NGS overnight at 4° C. The slides were then washed and counterstained in BM Purple (Roche).

Insulin Content and Secretion:

Cell clusters and islets were transferred to Eppendorf tubes and preincubated for 1 h in Krebs-Ringer buffer (KRB), followed by incubation for 2 hours in KRB containing 0.5 mM 1-isobutyl 3-methylxanthine (IBMX) and 16.7 mM glucose. Cell extract in acidic alcohol was used for determining C-peptide content. Human C-peptide levels were quantified using an ultrasensitive ELISA kit (Mercodia) according to the manufacturer's instructions (assay sensitivity is 1.5 pmol/L). The assay cross-reactivity with insulin and proinsulin is <0.0006% and <1.8%, respectively. Human proinsulin levels were quantified using a Proinsulin ELISA kit (Mercodia) according to the manufactures protocol (assay sensitivity is 0.5 μmol/L).

Statistical Analysis:

Significance was determined using two-tailed t-test and $\chi^2$ test. To approach a normal distribution of the qPCR data, a logarithmic transformation was preformed.

Results

To test the differentiation capacity of expanded islets cells, cells were transferred to serum-free medium (SFM), which has previously been shown to induce differentiation of expanded human islet cells [2,3]. This treatment resulted in cell cluster formation (FIG. 7C) and a modest, gradual increase in expression of insulin and other beta-cell transcripts during the 8-day incubation period (FIG. 7A). To screen for agents which induce further differentiation of expanded islets cells, a reporter lentivirus harboring an insulin promoter-DsRed2 gene (RIP-DsRed2) was used (FIG. 7B). Uncultured islet cells infected with this virus, which stably integrates into the host genome, express the fluorescent marker in all infected beta cells during the first days of culture, due to persistent insulin promoter activity. However, rapid dedifferentiation and loss of insulin promoter activity during cell expansion, coupled with the DsRed2 half-life of 4.5 days, results in marker disappearance (FIG. 7C). Following expansion, islet cells were transferred to SFM containing various agents, and differentiation was evaluated in live cells by scoring fluorescence reappearance. Based on preliminary screening of individual agents and their combinations, a two-step differentiation protocol was developed. In Step 1, expanded islet cells were transferred to SFM containing 25 mM Glucose, 1×N2, 1×B27, 1×ITS, 8 nM exendin-4, 4 nM activin A, and 100 µM nicotinamide for 6 days. In Step 2, the medium was changed for 2 days to the same medium without activin A and a reduced glucose concentration (5.6 mM). This treatment (termed Redifferentiation Cocktail, RC) resulted in cell cluster formation similar to that seen with SFM alone (FIG. 7C). However, quantitation by flow cytometry showed a 6-fold increase in the number of DsRed2$^+$ cells in the RC treatment, compared with SFM (FIG. 7D).

Since the expanded islet cell cultures represent a heterogeneous mix of several cell types, the observed differentiation could result from redifferentiation of dedifferentiated BCD cells, or de-novo differentiation of cells derived from other origins. To determine the cellular origin of the newly-generated insulin-expressing cells, the present inventors made use of an inducible lineage tracing approach (FIG. 7E). BCD cells in human islet cells were labeled during the first days of culture by infection with the RIP-Cre/ER and pTrip-loxP-NEO-STOP-loxP-eGFP lentivirus vectors in the presence of a tamoxifen (TM) pulse as previously described [12]. As seen in FIG. 12, Cre was specifically expressed in C-pep$^+$ cells. Labeled islet cells at p4 or p6 were treated with SFM or RC, respectively, and the differentiated cells were stained for human C-peptide and eGFP. Since the average beta-cell labeling efficiency is 57.5±8.9% [11], the excepted incidence of C-pep/eGFP-double-positive cells in case of redifferentiation should be approximately 50% percent, while de-novo differentiation should result in 0% co-labeling in the absence of TM. The actual incidence of double-positive cells found following SFM treatment was 60±16%, which is close to the expected value if redifferentiation is the predominant mechanism. However, the overall redifferentiation rate was relatively low, with 4.7±3.0% of all GFP$^+$ cells expressing C-peptide (1-2% of total cells, compared with <0.05% in control cells incubated in medium with serum). As observed with SFM alone, a large fraction (38±17%) of C-pep$^+$ cells co-stained for eGFP following RC treatment, indicating that generation of C-pep$^+$ cells under both culture conditions occurred primarily through redifferentiation of BCD cells.

Figure 8A:
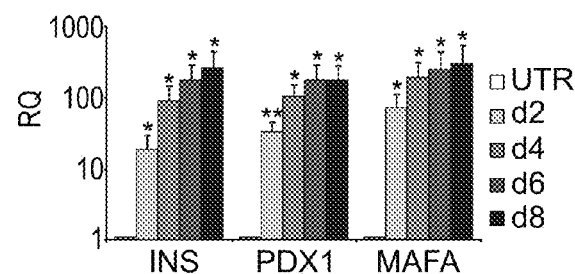
Figure 8D:
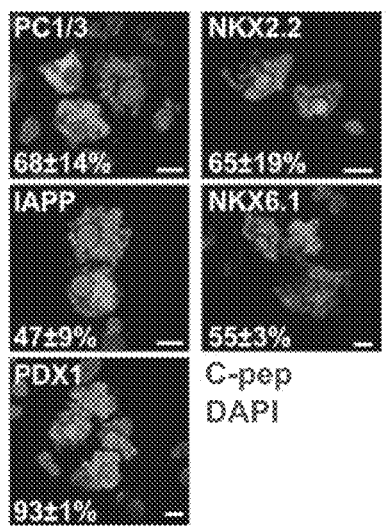
Figure 8B:
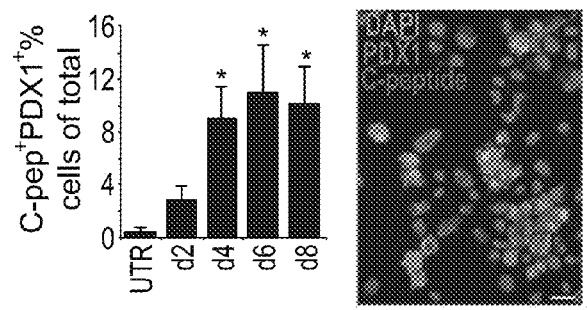
Figure 8C:
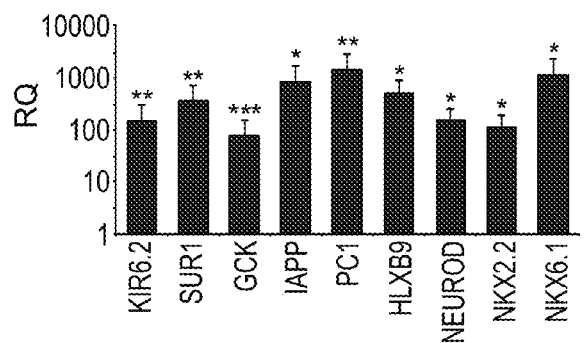
Figure 8E:
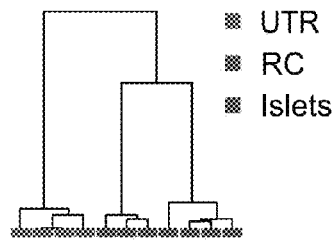

Redifferentiation Generates Beta-Like Cells:

Monitoring of redifferentiation in live cells with the RIP-DsRed2 reporter construct suggested that this process was gradual, starting from day 2 of treatment (data not shown). Gene expression analysis of RC-treated cells at different time points revealed a gradual increase in insulin expression, which confirmed the reliability of the fluorescent reporter (FIG. 8A). PDX1 and MAFA transcripts, encoding two transcription factors necessary for mature beta-cell function, increased over time similarly to insulin transcripts (FIG. 8A). To determine the kinetics of appearance C-pep$^+$ cells, cells treated with RC were co-stained every other day for C-peptide and PDX1 as markers of mature beta cells. As seen in FIG. 8B, the number of double-positive cells increased with time. This finding argues for a stochastic activation of the redifferentiation process, rather than a synchronized initial priming followed by further maturation. The differentiation rate peaked at 10.9±3.7% of total cells on day 6 and did not increase by day 8. This rate is 5-10-fold higher than that obtained with SFM alone. Given a fraction of ~40% BCD cells in the expanded cell population [11], this efficiency represents ~25% redifferentiation of BCD cells. Transcripts for the beta-cell transcription factors HBLX9, NEUROD, NKX2.2, and NKX6.1 were also strongly induced following 8 days of RC treatment (FIG. 8C). In addition, transcripts for KIR6.2, SUR1, GCK, IAPP and PC1/3, which are important for insulin maturation and secretion, were significantly upregulated, compared to untreated cells. Most of the redifferentiated cells co-expressed C-peptide and proteins essential for beta-cell function, including PDX1 (93±1%), NKX2.2 (65±19%), NKX6.1 (55±3%), IAPP (47±9%) and PC1/3 (68±14%). Microarray analysis of gene expression showed that RC treatment induced a global phenotypic change in expanded islet cells towards the phenotype of uncultured islet cells, as revealed by hierarchical cluster analyses (FIG. 8E). However, the RC-treated samples were still noticeably different from islet cells. This difference likely results from the partial redifferentiation (~25% of BCD cells) obtained with the RC treatment. Incubation of primary human fibroblasts or bone marrow-derived mesenchymal stem cells (BM-MSCs) in RC did not result in detectable insulin or PDX1 transcripts, further supporting the specific redifferentiation capacity of BCD cells.

Figure 9A:
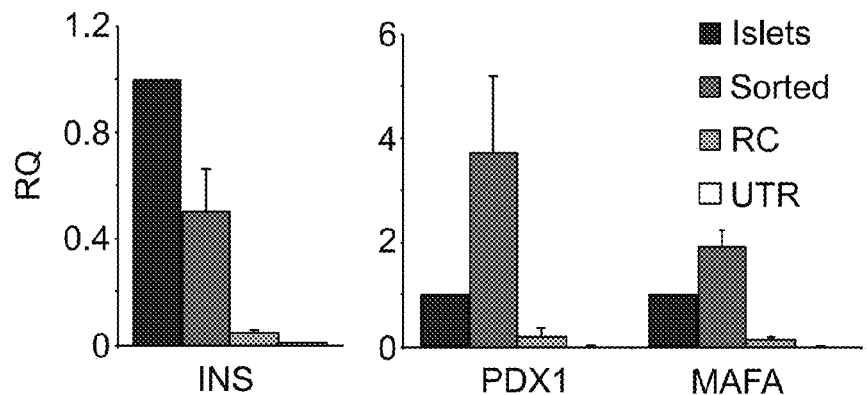
Figure 9B:
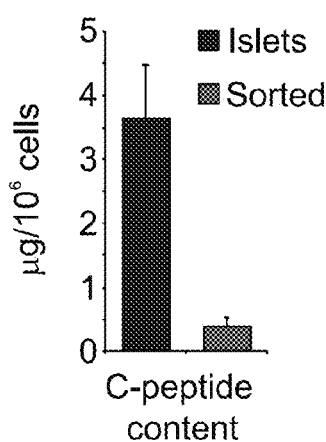
Figure 9C:
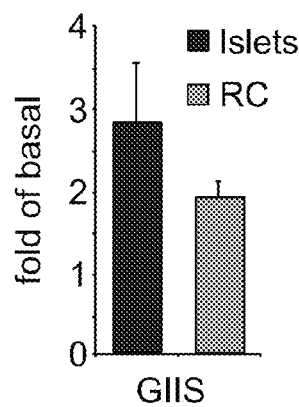
Figure 9D:
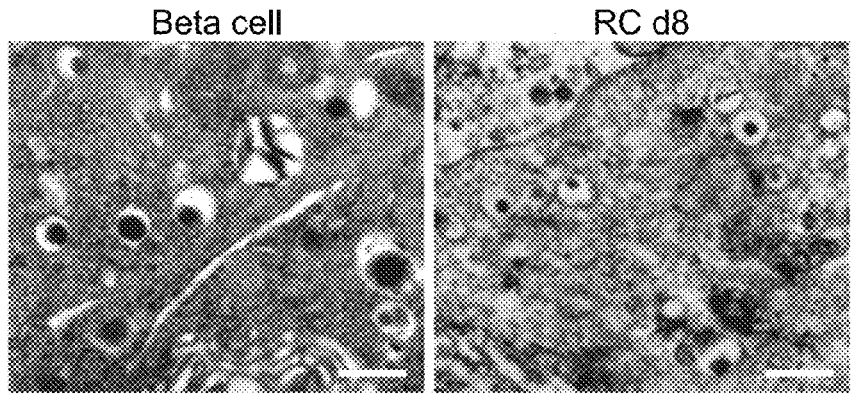

To characterize the redifferentiated cells in greater detail, expanded islet cells carrying the RIP-DsRed2 reporter gene were incubated with RC. After 8 days the formed cell clusters were dissociated, and cells were FACS-sorted and characterized. qPCR analysis of sorted DsRed2$^+$ cells detected levels of insulin transcripts averaging 50% of those present in isolated human islets (FIG. 9A). These levels represent approximately a 19-fold enrichment, compared to unsorted redifferentiated cells, and a 13,300-fold increase over untreated control cells (FIG. 9A). The levels of PDX1 and MAFA transcripts were comparable to those in human islets (FIG. 9A). In addition, sorted redifferentiated cells stored 10% of the C-peptide levels found in isolated human islets (FIG. 9B). Most of the insulin (~91%) was processed, as judged by human proinsulin-specific ELISA, which revealed only 9% proinsulin. When redifferentiated cells were challenged with 16.7 mM glucose and 0.5 mM 1-isobutyl 3-methylxanthine (IBMX), a 2-fold increase in insulin release was detected, compared with a 3-fold increase obtained with isolated human islets (FIG. 9C). Typical insulin vesicles were detected by electron microscopic analyses, although the dense-core insulin crystals appeared smaller, compared with those in human islets (FIG. 9D).

Redifferentiation is Associated with MET (Mesenchymal-Epithelial Transition):

Since beta cells undergo EMT (epithelial-mesenchymal transition) during culture initiation, the present inventors investigated whether BCD cell redifferentiation was associated with the reverse MET process. qPCR analysis revealed a significant upregulation of both transcripts and protein of the EMT effector SLUG (SNAI2) during dedifferentiation, and a small but significant downregulation during RC-induced redifferentiation (FIG. 10A-C). In contrast, no significant changes were noted in expression of SNAIL (SNAI1) (FIG. 10A,C) and TWIST (data not shown), two other transcription factors involved in EMT. Transcripts for the epithelial marker E-cadherin were significantly upregulated following RC treatment, while those encoding the mesenchymal marker N-cadherin were significantly reduced (FIG. 10D). In addition, while almost all expanded islet cells stained positive for the mesenchymal marker vimentin, upon redifferentiation C-pep$^+$ cells were vimentin-negative, and the incidence of vimentin$^+$ cells in the cell population decreased from 98±2% to 81±9% (FIG. 10E). Cells negative for both markers were also found, which could represent cells that turned off vimentin expression but have not yet activated insulin expression (FIG. 10E). These data indicate that redifferentiated BCD cells indeed transition from a mesenchymal to an epithelial phenotype.

Staining of the redifferentiated cells for the proliferation marker Ki67 did not detect positive cells, suggesting that cell differentiation in response to the RC treatment was accompanied by growth arrest (data not shown). To further validate this possibility, expanded islet cells were differentiated with RC in the presence of BrdU (for 7 out of 8 days). While control cells grown in regular expansion medium readily incorporated BrdU, BrdU-positive cells in cultures from 3 independent donors after the full 8-day course of differentiation were not found. In addition, only rare cells (0.9±0.6% based on counting >500 cells in each of 3 donors) were apoptotic following the full course of RC treatment, as determined by TUNEL assay (data not shown).

To further explore the role of SLUG downregulation in BCD cell redifferentiation, two SLUG shRNAs were employed to reduce SLUG expression beyond the small reduction (38±6%) induced by the RC treatment. Infection of expanded islet cells with SLUG shRNA lentiviruses reduced SLUG protein levels by ~70% (FIG. 10G). When combined with the RC treatment, two different SLUG shRNAs stimulated insulin transcript levels 12.4- and 5.5-fold, respectively, compared with scrambled shRNA (FIG. 10H), confirming the importance of SLUG downregulation for BCD cell redifferentiation.

BCD Cells Give Rise to Cells Expressing Other Islet Hormones:

In addition to losing insulin expression, the expanded islet cell populations are devoid of cells expressing the other 3 major islet hormones, glucagon, somatostatin, and pancreatic polypeptide (data not shown). The RC treatment resulted in appearance of immunostaining for each of these hormones in ~2% of the treated cells (FIG. 11A). No hormone co-expression was detected. To determine the origin of these cells, eGFP-labeled expanded cells were treated with RC for 8 days and co-stained for eGFP and the four islet hormones. As seen in FIG. 11A, the majority (91.8%) of eGFP$^+$ cells which activated islet hormone expression were redifferentiated into C-pep$^+$ cells. However, a small percent of them expressed instead one of the other islet hormones, most notably somatostatin (6.5%). These analyses suggested that at least part of the cells expressing islet hormones other than insulin were derived from BCD cells, raising the possibility that redifferentiating BCD transited through an islet progenitor-like stage. Analysis of expanded islet cells for transcripts of pancreas- and islet-progenitor cell transcription factors did not detect expression of PTF1A, TCF2, and PAX4 (Ct>40), and showed low but detectable levels of SOX9, FOXA2, and ARX transcripts. Following RC-induced redifferentiation, expression of some of these factors was significantly induced. Thus, SOX9 transcripts were upregulated 4-fold (FIG. 11B), and >20% of all expanded islet cells became SOX9' within 2 days of RC treatment (FIG. 11C). In addition, FOXA2, PAX4, and ARX were also significantly upregulated during this treatment (FIGS. 13A-B). Cells co-expressing SOX9 and vimentin could be detected, however SOX9 and C-peptide expression was mutually exclusive (FIG. 11D), suggesting a transient activation of SOX9 during redifferentiation and MET. SOX9 transcript levels were stimulated 5-fold by SLUG shRNA (FIG. 11E), suggesting that SOX9 expression is downstream of MET. CK19- or amylase-positive cells could not be detected following RC treatment (data not shown), suggesting that the expanded islet cells did not give rise to duct- or acinar-like cells.

Expression of NGN3 could not be reproducibly detected by qPCR. However, a significant increase in transcripts for INSM1 (FIG. 14), a direct target of NGN3 [13], was detected suggesting NGN3 expression. In the absence of a reliable NGN3 antibody, in-situ hybridization was performed to reveal the possible presence of NGN3$^+$ cells. This analysis revealed rare NGN3$^+$ cells on day 2 of the RC treatment, and increasing numbers on days 4, 6, and 8 (FIG. 11F), suggesting a transition through a NGN3$^+$ stage during BCD cell redifferentiation. No NGN3$^+$ cells were detected in expanded islet cells untreated with RC. Taken together, these findings suggest that BCD cell redifferentiation proceeds through an islet-progenitor-like stage, which may allow a low rate of differentiation into other islet cell types, in addition to insulin-producing cells, in particular the developmentally-related somatostatin-expressing cells. Transient SOX9 activation was detected during the adaptation of primary islet cells to proliferation in culture (FIG. 11G,H), suggesting that cell dedifferentiation also transits through a progenitor-like stage.

Discussion

The results presented herein, present an approach for expansion of insulin-producing cells from adult human islets in two steps, the first involving expansion of the mixed islet cell population, including ~40% dedifferentiated BCD cells, for up to 16 population doublings, followed by a second step of specific redifferentiation of BCD cells within the expanded islet cell population. The RC treatment employed achieved a remarkably reproducible differentiation in cells from all human donors tested. These conditions induce a profound phenotypic change in the expanded cells, which involves activation and shut-off of multiple genes. Lineage tracing suggests that the predominant source of newly-generated insulin-producing cells in these cultures is redifferentiation of BCD cells. The mixed islet cell cultures may contain cells expanded from mesenchymal stem cells (MSC) originally present in the islet preparation [14]; however the present inventors could not induce insulin expression with the RC treatment in non-BCD mesenchymal cell types, such as fibroblasts or BM-MSCs. The specific redifferentiation capacity of dedifferentiated BCD cells may be explained by a permissive epigenetic state ("epigenetic memory"). Thus, beta-cell genes may be poised for expression, however their lack of transcription may reflect an abnormal balance between transcription activators and repressors, and/or other chromatin modifications. Culture conditions in the redifferentiation medium may restore the proper balance without requirement for extensive epigenetic modifications.

Upon exposure to RC treatment BCD cells are depleted of growth factors present in the serum of the expansion medium, resulting in growth arrest. However, growth arrest by itself is not sufficient for induction of redifferentiation in expanded islet cells, as suggested by overexpression of the cell cycle inhibitor p57, which induces growth arrest without differentiation. The absence of serum also stimulates cell aggregation into islet-like clusters, which likely contributes to formation of cell conformation and cell-to-cell contacts required for BCD cell redifferentiation.

BCD cell redifferentiation involves MET, as judged by changes in gene expression, and by the stimulation of redifferentiation manifested following inhibition of the EMT effector SLUG using shRNA. It is possible that restoration of ECAD expression reinstates the normal cell-to-cell contacts needed for activation of beta-cell genes. Alternatively, transcription factors involved in EMT may act as repressors of beta-cell gene expression.

Treatment with RC induced redifferentiation of up to 25% of all BCD cells at p5-7. This represents a net 8-32 fold increase in the number of insulin-producing cells, compared to the uncultured islets.

The present inventors found open chromatin marks in beta-cell genes at the latest passage analyzed (p11). BCD cells induced to redifferentiate at p12 (representing up to 4096-fold expansion) showed an increase in insulin transcripts, when compared to untreated cells, which was comparable to that seen in earlier passages.

The generation of somatostatin-positive cells, and to a lesser extent glucagon- and pancreatic polypeptide-positive cells, from BCD cells suggests that redifferentiation involves transition through an islet progenitor-like stage. Activation of expression of transcription factors characteristic of islet progenitor cells during redifferentiation, including SOX9, FOXA2, PDX1, NGN3, PAX4, and ARX, supports this possibility. Nevertheless, the predominant hormone-producing cell type generated from BCD cells by the RC treatment is insulin-positive cells (91.8%), followed by somatostatin-positive cells (6.5%), and a small fraction of glucagon- and pancreatic polypeptide-positive cells (1.2% and 0.5%, respectively). It is intriguing to speculate that the epigenetic memory directs these transitory islet progenitor-like cells back into their cell type of origin, with some "leakage" into the developmentally-related somatostatin-positive cells. This culture system may provide an attractive model of human islet progenitor cell development, in which the cascade of transcription factor activation elucidated from mouse gene knockout models can be verified.

Example 3

Synergistic Effect of HES-1 Inhibition and Soluble Factors on Re-Differentiation of Expanded Pancreatic Beta Cells HES1 Inhibition and Redifferentiation Conditions—

HES1 shRNAs (accession numbers TRCN 18993) and a nontarget shRNA, both cloned in the pLKO.1 lentivirus vector, containing a puromycin-resistance gene, were obtained from the RNAi Consortium (Sigma-Aldrich). Virus was produced in 293T cells as previously described (Russ et al., (2009) PLoS One 4, e6417). Cells were infected at MOI 2.5:1 in growth medium containing 8 µg/ml polybrene overnight. The medium was then replaced with regular culture medium.

For redifferentiation experiments, expanded human islet cells or purified beta cell derived (BCD) cells at passages 5-7 were infected with HES1 shRNA or nontarget shRNA viruses. Two to four days following infection, cells were trypsinized, pelleted, and resuspended in either regular growth medium, SFM [CMRL 1066 containing 5.6 mM D-glucose and supplemented with 1% BSA fraction V (Sigma), insulin/transferrin/selenium (ITS) (Gibco-Invitrogen), penicillin (50 units/ml), and streptomycin (50 µg/ml)], or Redifferentiation Medium (RM) [SFM containing 25 mM D-glucose, and supplemented with 10 mM nicotinamide (Sigma), 8 nM exendin-4 (Acris), and 8 nM activin A (Peprotech)]. Cells were then seeded in tissue culture plates and incubated for the indicated periods. Medium was replaced every 2 days. Cells seeded in SFM or in RM formed clusters in culture. Cells were analyzed following 4-11 days of culture. In experiments conducted with RM, cells were seeded in ultra-low-attachment plates (Corning) at $3.2 \times 10^4/cm^2$ for improved aggregation.

qPCR Analyses—

Total RNA was extracted using RNAeasy Plus Micro Kit (Qiagen) or Trizol (Sigma-Aldrich) and treated with DNA-Free™ (Ambion). cDNA was prepared using High Capacity cDNA RT Kit (Applied Biosystems). qPCR was carried out in triplicates using TaqMan Universal PCR Master Mix (Applied Biosystems) or Universal Probe Library Master Mix (Roche) in 7300 Real-time PCR System (Applied Biosystems). Results were normalized to TATA-box-binding protein (TBP) and/or human large ribosomal protein (RPLPO) transcripts. Primer sequences are listed in Table 2, herein above. All reactions were performed with annealing at 60° C. for 40 cycles. For undetectable transcripts, the cycle number was set to 40 for comparisons.

Immunofluorescence Analyses—

Cells were trypsinized, spotted on slides using a Shandon Cytospin4 centrifuge (Thermo Scientific), and fixed for 15 min at room temperature in 4% paraformaldehyde (PFA). For BrdU staining slides were incubated in 1.5 M HCl for 20 min, followed by 0.1 M sodium borate (pH 8.5) for 10 min at RT and 3 washes in PBS. Samples were blocked for >10 min in blocking buffer (1% BSA, 5% fetal goat serum, and 0.2% saponin), and incubated 1 hour at room temperature or overnight at 4° C. with primary antibodies diluted in blocking buffer as follows: mouse anti-eGFP (1:500, Chemicon); rabbit anti-eGFP (1:1000, Invitrogen); mouse anti-human C-peptide (1:200, Biodesign); rabbit anti-human C-peptide (1:1000, Abcam); mouse anti-glucagon (1:2000, Sigma); rabbit anti-somatostatin (1:400, Dako); rabbit anti-human PDX1 (1:500, Abcam); mouse anti-NKX2.2 (1:1000, Hybridoma Bank), and mouse anti-BrdU (1:100, Chemicon). Slides were washed in PBST and incubated for 40 min with secondary antibodies conjugated to Alexa fluorophores (all from Invitrogen, 1:1000). Images were taken using a Leica SP5 confocal microscope. Images of living cells were taken with a Nikon microscope equipped with a NIS Elements camera and software. DNA was stained with DAPI.

Immunoblotting—

Cellular protein was extracted for 10 minutes in 1% NP40 containing protease inhibitor cocktail. Twenty µg protein were resolved on SDS-PAGE gel and electroblotted onto Immobilon-P membrane (Milipore), followed by incubation with rabbit anti-HES1 (Gift from T. Sudo, 1:1000) or rabbit anti-p57 (1:500, Santa Cruz). The bound antibody was visualized with appropriate horseradish peroxidase-conjugated anti-IgG (Jackson) and SuperSignal West Pico Chemiluminescent Substrate (Pierce). Quantification was done using TINA software.

In-Vivo Analyses—

Six-to-eight-week-old nonobese diabetic-severe combined immunodeficient (NOD-SCID) mice were made hyperglycemic (blood glucose level above 300 mg/dl) by a single i.p. injection of 180 µg streptozotocin (STZ) (Acros Organics) per gr body weight. Expanded human islet cells at passage 5 were infected with HES1 shRNA or nontarget shRNA, and 2 days later $2 \times 10^6$ cells were injected under the kidney capsule of mice considered hyperglycemic, using a 30-gauge needle. Glucose levels of transplanted mice were monitored once a week in blood samples obtained from the tail vein using Accutrend strips (Roche diagnostic). Serum human C-peptide was determined in blood samples obtained from the orbital plexus of fed mice by C-peptide ELISA (Millipore) according to the manufacturer's protocol. Serum obtained from untreated mice was used as control. Mice were sacrificed 56 days post-transplantation, and the kidney was removed. Part of the transplant area was embedded in paraffin and sectioned for histological analyses, while another part was transferred into TRI©Reagent (Sigma-Aldrich) and homogenized using pellet pestle. RNA was extracted according to the manufacturer's protocol. cDNA production and qPCR were executed as described above. RNA extracted from kidney of untreated mice served as control. Results were normalized to human glyceraldehyde-3-phosphate dehydrogenase (GAPDH) transcripts. Paraffin sections (5 μm) were deparaffinized and rehydrated, and antigen retrieval was performed before staining. Sections were blocked for 10 minutes in CAS-BLOCK (Zymed), incubated overnight at 4° C. with mouse anti-human C-peptide (1:200, Biodesign) or guinea pig anti-insulin (1:200, Dako), washed 3 times in PBS, incubated 30 min at room temperature with the appropriate secondary biotin-bound antibody (Enco), washed in PBS, and incubated for 15 minutes at room temperature with avidin-HRP (Sigma). Color was developed using the DAB Chromogen kit (Zymed) according to manufacturer's instructions, and counter-staining was performed using hematoxylin. Sections were dehydrated, mounted with Entellan (Merck), and viewed under TE-200 microscope.

Statistical Analysis—

Significance was determined using Student's t test. To approach a normal distribution of the qPCR data, a logarithmic transformation was performed. The Bonferroni correction was applied to account for multiple testing.

Results

The present inventors combined HES1 inhibition and SFM-induced cell aggregation with the addition of soluble factors that have been shown to contribute to β-cell differentiation in vitro. SFM containing soluble factors, termed Redifferentiation Medium (RM), included, in addition to 1% BSA and ITS, nicotinamide (10 mM), high glucose (increased from 5.6 mM in the growth medium to 25 mM), activin A (4 nM), and the glucagon-like peptide 1 analog exendin-4 (8 nM). Low-adherence plates were used instead of regular culture plates to enhance cell cluster formation. Sorted eGFP$^+$ cells at passages 5-6 were infected with HES1 shRNA or nontarget shRNA viruses, and 4 days later were seeded in RM or growth medium for an additional 4-day period. qPCR analysis showed a significant additive effect of the combined treatment, compared to HES1 inhibition or RM treatment alone. RM treatment alone increased INS transcript levels 23.5±10.5-fold, compared with eGFP$^+$ cells in growth medium (p=0.12) (FIG. 15A). In contrast, the combined treatment of RM and HES1 shRNA lead to an increase of 144.2±29.7-fold (p=0.01). Thus, INS expression in the combined treatment was 6.1-fold (p=0.04) higher compared to RM treatment alone. Levels of PDX1 transcripts were 5.5-fold higher in eGFP$^+$ cells treated with the combined treatment, compared with eGFP$^+$ cells treated with RM alone (p=0.03). Transcript levels for other islet hormones were also upregulated following the combined treatment. GCG, SST and PPY transcript levels were 2.5- (p=0.2), 3.4- (p=0.04), and 5.2-fold (p=0.01) higher, respectively, in eGFP$^+$ cells treated with RM and HES1 shRNA, compared with cells treated with RM alone (FIG. 15A). To further validate these findings, eGFP-labeled expanded islet cells were infected at passage 5 with HES1 shRNA or nontarget viruses. Cells were seeded in RM in low-attachment plates 2 days following infection, and costained for eGFP and C-peptide 4 days later (FIG. 15B). Fifteen percent of eGFP$^+$ cells in the HES1 shRNA-infected population treated with RM were redifferentiated, as judged by C-peptide staining, compared with 6.8% in the nontarget shRNA-infected group treated with RM (based on quantitation of 500 cells in each group). No C-peptide-positive cells were found in the untreated cell population. Thus, HES1 inhibition potentiated the effect of RM 2.2-fold. In both groups about 80% of the C-peptide-positive cells were also positive for eGFP$^+$. Since the average labeling efficiency is 57.5±8.9%, this result indicates that most or all the C-peptide-positive cells were derived from BCD cells.

Phenotype of Redifferentiated Cells Following HES1 shRNA and RM Treatment.

The same experiment described in the previous section was repeated using unlabeled cells, to allow co-staining for multiple antigens using different fluorescent dyes. Co-staining of the redifferentiated cells for C-peptide and the islet hormones GCG and SST did not reveal any co-expression of these hormones (FIG. 15C). While 19.9±6.4% of the cells in the HES1 shRNA/RM group were positive for C-peptide, only 7.7±2.2% of the cells were C-peptide-positive in the nontarget/RM group (FIG. 15D). Thus, HES1 inhibition potentiated the effect of RM in this experiment 2.6-fold. Given that BCD cells represent ~40% of total expanded islet cells, differentiation of about 20% of total islet cells with the HES1 shRNA/RM treatment represents redifferentiation of ~50% of BCD cells, which is double the 25% obtained with soluble factors alone. Only 2.1±0.9% of the cells in the HES1 shRNA/RM group, and 1.8±1.3% of the cells in the nontarget/RM group were positive for GCG. Similarly, only 0.9±0.2% and 1.3±0.7% were positive for SST in the HES1 shRNA/RM group and the nontarget/RM group, respectively. Cells expressing the islet hormone PPY were rare in both groups. The transcription factors PDX1 and NKX2.2 are important for β-cell development and function. Co-staining for PDX1 or NKX2.2 and C-peptide showed that all the C-peptide-positive cells expressed these markers in their nucleus, following the combined treatment of HES1 shRNA and RM (FIG. 15E).

To evaluate cell mortality rates following redifferentiation, TUNEL assay for apoptosis detection was performed on cells from 3 donors following the combined treatment. Results revealed significant differences between the HES1 shRNA/RM group and the nontarget shRNA/RM group, averaging 12.0±4.6% and 7.1±3.7% (p=0.045) apoptotic cells, respectively (images not shown). Thus, the additive effect of HES1 inhibition on cell mortality was 5%.

Expanded Islet Cells Redifferentiated by HES1 Inhibition Corrected Hyperglycemia in Immunodeficient Mice.

Figure 16D:
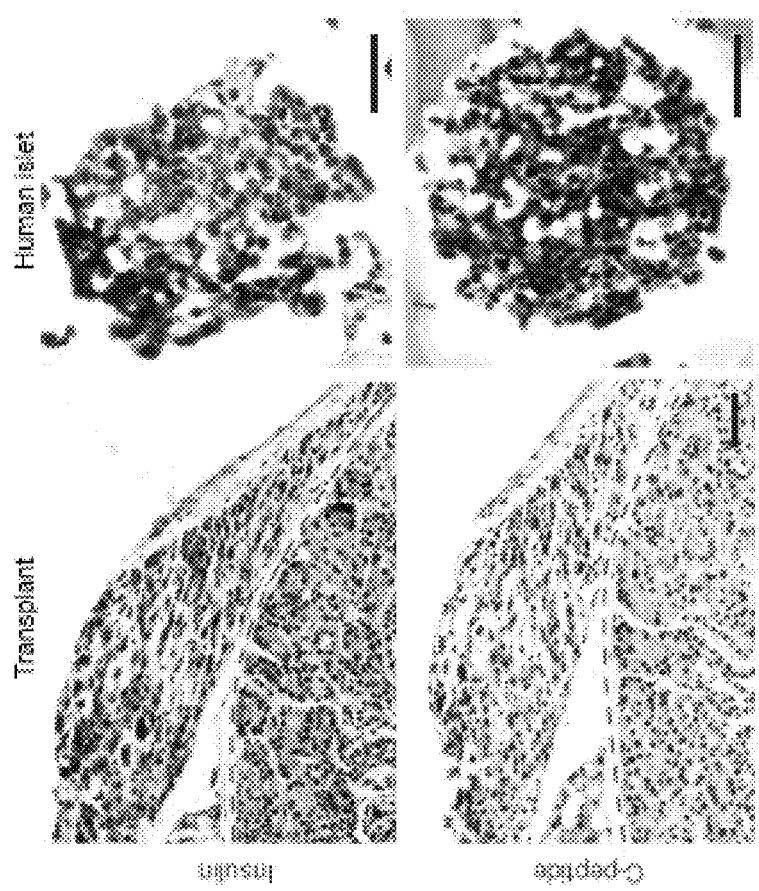

Human islet cells at passage 5 were infected with HES1 shRNA or nontarget viruses, and transplanted 4 days later under the kidney capsule of STZ-treated hyperglycemic NOD-SCID mice. Six mice were transplanted with HES1-inhibited cells, and 5 mice were transplanted with control cells. The mice were kept for 56 days. During this period all the control mice, and 3/6 of the experimental mice, exhibited blood glucose levels >600 mg/dL and eventually died. However, 3/6 of the experimental mice survived. These mice showed decreased blood glucose levels (FIG. 16A), as well as human C-peptide in their serum, averaging 0.4±0.2 ng/ml (FIG. 16B). The mice were sacrificed at the end of the experiment, and the transplants were recovered for RNA and immunohistochemical analyses. qPCR analyses using human-specific primers revealed a 298±140-fold increase in human INS transcripts in the transplanted cells, compared with cultured cells infected with nontarget virus (FIG. 16C). For comparison, the increase in INS mRNA induced by HES1 shRNA in these cells in culture was only 4.4±3.2-fold (FIG. 16C). Thus, transplantation induced a further 68-fold increase in INS transcripts. Immunohistochemical analyses revealed the presence of insulin and C-peptide in the transplanted cells (FIG. 16D). Thus, treatment with HES1 shRNA is sufficient for priming expanded islet cells for further differentiation in vivo into functional beta-like cells, which are capable of correcting glycemia in hyperglycemic mice.

REFERENCES FOR EXAMPLE 2

1. Hayek A, Beattie G M, Cirulli V, Lopez A D, Ricordi C, Rubin J S. Growth factor/matrix-induced proliferation of human adult beta-cells. *Diabetes* 1995. 44:1458-1460.

2. Gershengorn M C, Hardikar A A, Wei C, Geras-Raaka E, Marcus-Samuels B, Raaka B M. Epithelial-to-mesenchymal transition generates proliferative human islet precursor cells, *Science* 2004. 306:2261-2264.
3. Lechner A, Nolan A L, Blacken R A, Habener J F. Redifferentiation of insulin-secreting cells after in vitro expansion of adult human pancreatic islet tissue. *Biochem Biophys Res Commun* 2005. 327:581-588.
4. Ouziel-Yahalom L, Zalzman M, Anker-Kitai L, Knoller S, Bar Y, Glandt M, Herold K, Efrat S. Expansion and redifferentiation of adult human pancreatic islet cells. *Biochem Biophys Res Commun* 2006. 341:291-298.
5. Parnaud G, Bosco D, Berney T Pattou F, Kerr-Conte J, Donath M Y, Bruun C, Mandrup-Poulsen T, Billestrup N, Halban P A. Proliferation of sorted human and rat beta cells. *Diabetologia* 2008. 51:91-100
6. Meier J J, Bhushan A, Butler A E, Rizza R A, Butler P C. Sustained beta-cell apoptosis in patients with long-standing type 1 diabetes: indirect evidence for islet regeneration? *Diabetologia* 2005. 48:2221-2228.
7. Butler A E, Janson J, Bonner-Weir S, Ritzel R, Rizza R A, Butler P C. Beta cell deficit and increased beta-cell apoptosis in humans with type 2 diabetes. *Diabetes* 2003. 52:102-110.
8. Meier J J, Butler A E, Saisho Y, Monchamp T, Galasso R, Bhushan A, Rizza R A, Butler P C. Beta-cell replication is the primary mechanism subserving the postnatal expansion of beta-cell mass in humans. *Diabetes* 2008. 57:1584-1594.
9. 20. Nielsen J H, Brunstedt J, Andersson A, Frimodt-Møller C. Preservation of beta cell function in adult human pancreatic islets for several months in vitro. *Diabetologia* 1979. 16:97-100.
10. Nielsen J H, Galsgaard E D, Moldrup A, Friedrichsen B N, Billestrup N, Hansen J A, Lee Y C, Carlsson C. Regulation of beta-cell mass by hormones and growth factors. *Diabetes* 2001. 50(Suppl 1):S25-S29.
11. Russ H A, Bar Y, Ravassard P, Efrat S. In vitro proliferation of cells derived from adult human beta cells revealed by cell-lineage tracing. *Diabetes* 2008. 57:1575-1583.
12. Russ H A, Ravassard P, Kerr-Conte J, Pattou F, Efrat S. Epithelial-mesenchymal transition in cells expanded in vitro from lineage-traced adult human pancreatic beta cells. *PLoS ONE* 2009. 4:e6417.
13. Mellitzer G, Bonné S, Luco R F, Van De Casteele M, Lenne-Samuel N, Collombat P, Mansouri A, Lee J, Lan M, Pipeleers D, Nielsen F C, Ferrer J, Gradwohl G, Heimberg H. IA1 is NGN3-dependent and essential for differentiation of the endocrine pancreas. *EMBO J* 2006. 25:1344-1352.
14. Davani B, Ikonomou L, Raaka B M, Geras-Raaka E, Morton R A, Marcus-Samuels B, Gershengorn M C. Human islet-derived precursor cells are mesenchymal stromal cells that differentiate and mature to hormone-expressing cells in vivo. *Stem Cells* 2007. 25:3215-3222.
15. Smukler S R, Arntfield M E, Razavi R, Bikopoulos G, Karpowicz P, Seaberg R, Dai F, Lee S, Ahrens R, Fraser P E, Wheeler M B, van der Kooy D. The adult mouse and human pancreas contain rare multipotent stem cells that express insulin. *Cell Stem Cell* 2011. 8:281-293.

REFERENCES FOR MATERIALS AND METHODS

1. Ouziel-Yahalom L, Zalzman M, Anker-Kitai L, Knoller S, Bar Y, Glandt M, Herold K, Efrat S. Expansion and redifferentiation of adult human pancreatic islet cells. *Biochem Biophys Res Commun* 2006. 341:291-298.
2. Russ H A, Bar Y, Ravassard P, Efrat S. In vitro proliferation of cells derived from adult human beta cells revealed by cell-lineage tracing. *Diabetes* 2008. 57:1575-1583.
3. Bar Y, Russ H A, Knoller S, Ouziel-Yahalom L, Efrat S. HES1 is involved in adaptation of adult human beta cells to proliferation in vitro. *Diabetes* 2008. 57:2413-2420.
4. Russ H A, Ravassard P, Kerr-Conte J, Pattou F, Efrat S. Epithelial-mesenchymal transition in cells expanded in vitro from lineage-traced adult human pancreatic beta cells. *PLoS ONE* 2009. 4:e6417.
5. Karnieli O, Izhar-Prato Y, Bulvik S, Efrat S. Generation of insulin-producing cells from human bone marrow mesenchymal stem cells by genetic manipulation. *Stem Cells* 2007. 25: 2837-2844.
6. Yaron O, Farhy C, Marquardt T, Applebury M, Ashery-Padan R. Notch1 functions to suppress cone-photoreceptor fate specification in the developing mouse retina. *Development* 2006. 133:1367-1378.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of ex-vivo increasing insulin content in progenitor cells which express SLUG, comprising:
   (a) expanding adult islet beta cells to generate dedifferentiated adult islet beta cells; and subsequently
   (b) contacting said dedifferentiated adult islet beta cells with an siRNA or shRNA agent which is directed against SLUG, thereby increasing insulin content in the progenitor cells.

2. The method of claim 1, wherein said culturing expanding is effected in CMRL medium.

3. The method of claim 1, wherein said adult islet beta cells are trypsinized.

4. The method of claim 1, further comprising
   (a) exposing the adult islet beta cells to a culture medium comprising nicotinamide, exendin-4, and activin A, wherein glucose is present at a concentration of 10-100 mM; wherein said culture medium is devoid of serum; and subsequently
   (b) exposing said adult islet beta cells to an additional culture medium comprising nicotinamide and exendin-4, wherein glucose is present at a concentration of 0.5-10 mM, wherein said additional medium is devoid of activin A, wherein steps (a) and (b) are effected prior to said contacting and following said expanding.

* * * * *